(12) United States Patent
Salman et al.

(10) Patent No.: US 11,234,581 B2
(45) Date of Patent: Feb. 1, 2022

(54) ELEVATOR FOR DIRECTING MEDICAL TOOL

(71) Applicant: EndoChoice, Inc., Alpharetta, GA (US)

(72) Inventors: Golan Salman, Atlit (IL); Moshiko Levi, Ganey Tikva (IL)

(73) Assignee: EndoChoice, Inc., Alpharetta, GA (US)

( * ) Notice: Subject to any disclaimer, the term of this patent is extended or adjusted under 35 U.S.C. 154(b) by 820 days.

(21) Appl. No.: 14/701,805

(22) Filed: May 1, 2015

(65) Prior Publication Data

US 2015/0313451 A1 Nov. 5, 2015

Related U.S. Application Data

(60) Provisional application No. 61/988,084, filed on May 2, 2014.

(51) Int. Cl.
*A61B 1/00* (2006.01)
*A61B 1/018* (2006.01)
(Continued)

(52) U.S. Cl.
CPC ...... *A61B 1/00098* (2013.01); *A61B 1/00066* (2013.01); *A61B 1/00181* (2013.01);
(Continued)

(58) Field of Classification Search
CPC ............ A61B 1/00087; A61B 1/00096; A61B 1/00098; A61B 1/012; A61B 1/125;
(Continued)

(56) References Cited

U.S. PATENT DOCUMENTS 3,871,365 A * 3/1975 Chikama ............ A61B 1/00183
600/107
3,896,793 A * 7/1975 Mitsui ................ A61B 1/00098
600/104

(Continued)

FOREIGN PATENT DOCUMENTS

CA 2297986 3/1999
CA 2765559 12/2010

(Continued)

OTHER PUBLICATIONS

Corrected Notice of Allowance dated Apr. 13, 2016 for U.S. Appl. No. 13/680,646.

(Continued)

*Primary Examiner* — Ryan N Henderson
(74) *Attorney, Agent, or Firm* — Bookoff McAndrews, PLLC

(57) ABSTRACT

There is provided herein an endoscope assembly comprising at least one front-pointing viewing element on a front end of a distal section of the endoscope assembly, at least one side-looking viewing element on at least one side wall of the distal section of the endoscope assembly, a working channel configured for insertion of a medical tool towards the distal section, and a system for regulating the direction of exit of medical device wherein said system enables the medical device to exit at multiple angles to the long dimension of the endoscope device either from the front end or through side walls of the distal section of the device.

9 Claims, 10 Drawing Sheets

(51) Int. Cl.
*A61B 1/05* (2006.01)
*A61B 1/06* (2006.01)

(52) U.S. Cl.
CPC .............. *A61B 1/018* (2013.01); *A61B 1/051* (2013.01); *A61B 1/0676* (2013.01); *A61B 1/0684* (2013.01)

(58) Field of Classification Search
CPC . A61B 1/128; A61B 1/00174; A61B 1/00177; A61B 1/00179; A61B 1/00181; A61B 1/00183; A61B 1/273; A61B 1/2733; A61B 1/2736; A61B 1/00193
See application file for complete search history.

(56) References Cited

U.S. PATENT DOCUMENTS

| | | | |
|---|---|---|---|
| 3,915,157 A * | 10/1975 | Mitsui | A61B 1/018 600/107 |
| 3,924,608 A * | 12/1975 | Mitsui | A61B 1/00098 600/107 |
| 4,027,697 A | 6/1977 | Bonney | |
| 4,084,401 A | 4/1978 | Belardi | |
| 4,224,929 A * | 9/1980 | Furihata | A61B 1/00082 600/107 |
| 4,402,313 A | 9/1983 | Yabe | |
| 4,407,273 A * | 10/1983 | Ouchi | A61B 1/00098 600/107 |
| 4,427,000 A * | 1/1984 | Ueda | A61B 17/29 600/107 |
| 4,452,236 A * | 6/1984 | Utsugi | A61M 25/0147 600/107 |
| 4,461,282 A | 7/1984 | Ouchi | |
| 4,494,549 A | 1/1985 | Namba | |
| 4,532,918 A | 8/1985 | Wheeler | |
| 4,588,294 A | 5/1986 | Siegmund | |
| 4,589,403 A * | 5/1986 | Ouchi | A61B 1/126 600/104 |
| 4,593,680 A * | 6/1986 | Kubokawa | A61B 1/00098 600/104 |
| 4,641,635 A | 2/1987 | Yabe | |
| 4,646,722 A * | 3/1987 | Silverstein | A61B 1/00073 600/104 |
| 4,697,576 A * | 10/1987 | Krauter | A61B 1/018 600/107 |
| 4,727,859 A | 3/1988 | Lia | |
| 4,764,001 A | 8/1988 | Yokota | |
| 4,801,792 A | 1/1989 | Yamasita | |
| 4,825,850 A | 5/1989 | Opie | |
| 4,841,949 A * | 6/1989 | Shimizu | A61B 1/00098 600/107 |
| 4,868,644 A * | 9/1989 | Yabe | A61B 1/0052 348/76 |
| 4,870,951 A * | 10/1989 | Suzuki | A61B 1/00098 600/130 |
| 4,877,314 A | 10/1989 | Kanamori | |
| 4,902,115 A | 2/1990 | Takahashi | |
| 4,949,706 A * | 8/1990 | Thon | A61B 1/00098 600/104 |
| 4,976,522 A | 12/1990 | Igarashi | |
| 4,984,878 A | 1/1991 | Miyano | |
| 5,007,406 A | 4/1991 | Takahashi | |
| 5,014,685 A | 5/1991 | Takahashi | |
| 5,097,838 A * | 3/1992 | Hirooka | A61B 1/00098 600/463 |
| 5,193,525 A | 3/1993 | Silverstein | |
| 5,224,929 A | 7/1993 | Remiszewski | |
| 5,296,971 A | 3/1994 | Mori | |
| 5,325,847 A * | 7/1994 | Matsuno | A61B 1/0011 600/107 |
| 5,343,853 A * | 9/1994 | Komi | A61B 1/00098 600/107 |
| 5,359,456 A | 10/1994 | Kikuchi | |
| 5,395,329 A | 3/1995 | Fleischhacker | |
| 5,447,148 A | 9/1995 | Oneda | |
| 5,460,167 A * | 10/1995 | Yabe | A61B 1/00098 600/107 |
| 5,460,168 A * | 10/1995 | Masubuchi | A61B 1/00142 600/123 |
| 5,464,007 A | 11/1995 | Krauter | |
| 5,489,256 A | 2/1996 | Adair | |
| 5,518,501 A | 5/1996 | Oneda | |
| 5,518,502 A | 5/1996 | Kaplan | |
| 5,547,457 A | 8/1996 | Tsuyuki | |
| 5,562,600 A * | 10/1996 | Matsuno | A61B 1/00098 600/107 |
| 5,569,157 A * | 10/1996 | Nakazawa | A61B 1/0008 600/104 |
| 5,569,162 A * | 10/1996 | Komi | A61B 1/00098 600/129 |
| 5,573,494 A * | 11/1996 | Yabe | A61B 1/00091 600/104 |
| 5,575,755 A | 11/1996 | Krauter | |
| 5,587,839 A | 12/1996 | Miyano | |
| 5,630,782 A | 5/1997 | Adair | |
| 5,662,588 A * | 9/1997 | Iida | A61B 1/00091 600/121 |
| 5,674,181 A * | 10/1997 | Iida | A61B 1/0008 600/127 |
| 5,674,182 A | 10/1997 | Suzuki | |
| 5,685,823 A | 11/1997 | Ito | |
| 5,702,347 A | 12/1997 | Yabe | |
| 5,707,344 A * | 1/1998 | Nakazawa | A61B 1/0008 600/107 |
| 5,725,474 A | 3/1998 | Yasui | |
| 5,725,476 A | 3/1998 | Yasui | |
| 5,725,477 A | 3/1998 | Yasui | |
| 5,725,478 A | 3/1998 | Saad | |
| 5,730,701 A * | 3/1998 | Furukawa | A61B 1/0008 600/121 |
| 5,777,797 A | 7/1998 | Miyano | |
| 5,782,751 A | 7/1998 | Matsuno | |
| 5,810,715 A | 9/1998 | Moriyama | |
| 5,836,894 A | 11/1998 | Sarvazyan | |
| 5,860,913 A * | 1/1999 | Yamaya | A61B 1/00091 600/127 |
| 5,865,726 A * | 2/1999 | Katsurada | A61B 1/12 600/127 |
| 5,868,663 A * | 2/1999 | Katsurada | A61B 1/018 600/107 |
| 5,870,234 A | 2/1999 | EbbesmeierneeSchitthof | |
| 5,916,148 A | 6/1999 | Tsuyuki | |
| 5,940,126 A | 8/1999 | Kimura | |
| 6,095,970 A | 8/2000 | Hidaka | |
| 6,117,068 A | 9/2000 | Gourley | |
| 6,181,481 B1 | 1/2001 | Yamamoto | |
| 6,196,967 B1 | 3/2001 | Lim | |
| 6,238,336 B1 * | 5/2001 | Ouchi | A61B 1/00098 600/104 |
| 6,261,226 B1 | 7/2001 | McKenna | |
| 6,277,064 B1 | 8/2001 | Yoon | |
| 6,338,717 B1 * | 1/2002 | Ouchi | A61B 1/00082 600/461 |
| 6,359,674 B1 | 3/2002 | Horiuchi | |
| 6,375,610 B2 | 4/2002 | Verschuur | |
| 6,390,973 B1 * | 5/2002 | Ouchi | A61B 1/00098 600/104 |
| 6,402,738 B1 | 6/2002 | Ouchi | |
| 6,419,626 B1 | 7/2002 | Yoon | |
| 6,458,074 B1 * | 10/2002 | Matsui | A61B 1/00098 600/104 |
| 6,476,851 B1 | 11/2002 | Nakamura | |
| 6,605,033 B1 * | 8/2003 | Matsuno | A61B 1/00098 600/106 |
| 6,638,214 B2 | 10/2003 | Akiba | |
| 6,673,012 B2 | 1/2004 | Fujii | |
| 6,712,760 B2 | 3/2004 | Sano | |
| 6,832,984 B2 | 12/2004 | Stelzer | |
| 6,888,119 B2 | 5/2005 | Iizuka | |
| 7,435,218 B2 | 10/2008 | Krattiger | |
| 7,621,869 B2 | 11/2009 | Ratnakar | |

(56) References Cited

U.S. PATENT DOCUMENTS

| | | |
|---|---|---|
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,927,272 B2 | 4/2011 | Bayer |
| 7,967,745 B2 | 6/2011 | Gilad |
| 7,976,462 B2 | 7/2011 | Wright |
| 8,038,604 B2 * | 10/2011 | Hamazaki ........ A61B 1/00142 600/127 |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,313,427 B2 * | 11/2012 | Ishii .................. A61B 1/0011 600/170 |
| 8,447,132 B1 | 5/2013 | Galil |
| 8,449,457 B2 | 5/2013 | Aizenfeld |
| 8,545,394 B2 * | 10/2013 | Motai ................ A61B 1/0051 600/104 |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,314,147 B2 | 4/2016 | Levy |
| 9,320,419 B2 | 4/2016 | Kirma |
| 2001/0036322 A1 | 11/2001 | Bloomfield |
| 2001/0044570 A1 * | 11/2001 | Ouchi ................ A61B 1/00098 600/107 |
| 2002/0017515 A1 | 2/2002 | Obata |
| 2002/0047897 A1 | 4/2002 | Sugimoto |
| 2002/0087047 A1 | 7/2002 | Remijan |
| 2002/0087100 A1 * | 7/2002 | Onuki ................ A61B 1/00098 600/585 |
| 2002/0091303 A1 * | 7/2002 | Ootawara ................ A61B 1/01 600/106 |
| 2002/0109774 A1 | 8/2002 | Meron |
| 2002/0161281 A1 | 10/2002 | Jaffe |
| 2002/0172498 A1 | 11/2002 | Esenyan |
| 2002/0183591 A1 | 12/2002 | Matsuura |
| 2002/0193741 A1 * | 12/2002 | Secrest .............. A61B 17/3478 604/164.06 |
| 2003/0030918 A1 | 2/2003 | Murayama |
| 2003/0063398 A1 | 4/2003 | Abe |
| 2003/0073955 A1 * | 4/2003 | Otawara ............ A61B 1/00098 604/164.01 |
| 2003/0076411 A1 | 4/2003 | Iida |
| 2003/0083552 A1 | 5/2003 | Remijan |
| 2003/0128893 A1 | 7/2003 | Castorina |
| 2003/0153897 A1 | 8/2003 | Russo |
| 2004/0015054 A1 | 1/2004 | Hino |
| 2004/0046865 A1 | 3/2004 | Ueno |
| 2004/0049095 A1 * | 3/2004 | Goto .................... A61B 1/018 600/107 |
| 2004/0061780 A1 | 4/2004 | Huffman |
| 2004/0082836 A1 * | 4/2004 | Hino .................. A61B 1/0008 600/170 |
| 2004/0106850 A1 * | 6/2004 | Yamaya ............ A61B 1/00098 600/107 |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0049455 A1 * | 3/2005 | Ootawara .......... A61B 1/00098 600/107 |
| 2005/0090709 A1 * | 4/2005 | Okada .................... A61B 1/042 600/104 |
| 2005/0096501 A1 | 5/2005 | Stelzer |
| 2005/0101836 A1 * | 5/2005 | Onuki ................ A61B 1/00137 600/104 |
| 2005/0119527 A1 | 6/2005 | Banik |
| 2005/0222493 A1 * | 10/2005 | Kohno ............... A61B 1/00098 600/107 |
| 2005/0228289 A1 * | 10/2005 | Kohno ..................... A61B 8/14 600/463 |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0283048 A1 | 12/2005 | Gill |
| 2006/0047184 A1 | 3/2006 | Banik |
| 2006/0063976 A1 | 3/2006 | Aizenfeld |
| 2006/0069314 A1 | 3/2006 | Farr |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235271 A1 * | 10/2006 | Carter .................... A61B 1/018 600/107 |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0099500 A1 * | 5/2007 | Pilvisto ............. A61B 1/00098 439/584 |
| 2007/0106119 A1 | 5/2007 | Hirata |
| 2007/0112249 A1 * | 5/2007 | Yamaya ................ A61B 1/018 600/107 |
| 2007/0118019 A1 * | 5/2007 | Mitani .................... A61B 1/051 600/176 |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197871 A1 * | 8/2007 | Geitz ................. A61B 1/00098 600/117 |
| 2007/0197875 A1 | 8/2007 | Osaka |
| 2007/0203396 A1 | 8/2007 | McCutcheon |
| 2007/0206945 A1 | 9/2007 | Delorme |
| 2007/0208219 A1 * | 9/2007 | Carter ................ A61B 1/00177 600/107 |
| 2007/0208220 A1 * | 9/2007 | Carter ................ A61B 1/00098 600/107 |
| 2007/0208221 A1 * | 9/2007 | Kennedy, II ....... A61B 1/00098 600/107 |
| 2007/0213591 A1 | 9/2007 | Aizenfeld |
| 2007/0229656 A1 | 10/2007 | Khait |
| 2007/0232857 A1 * | 10/2007 | Otawara ............ A61B 1/00177 600/129 |
| 2007/0244353 A1 | 10/2007 | Larsen |
| 2007/0244354 A1 | 10/2007 | Bayer |

(56) References Cited

U.S. PATENT DOCUMENTS

| | | | |
|---|---|---|---|
| 2007/0244355 A1* | 10/2007 | Shaw | A61B 1/00133 600/107 |
| 2007/0244356 A1* | 10/2007 | Carrillo, Jr. | A61B 1/018 600/107 |
| 2007/0247867 A1 | 10/2007 | Hunter | |
| 2007/0249898 A1* | 10/2007 | Otawara | A61B 1/00098 600/107 |
| 2007/0265492 A1 | 11/2007 | Sonnenschein | |
| 2007/0265494 A1* | 11/2007 | Leanna | A61B 1/00098 600/107 |
| 2007/0270638 A1* | 11/2007 | Kitano | A61B 1/00098 600/104 |
| 2007/0270642 A1 | 11/2007 | Bayer | |
| 2007/0279486 A1 | 12/2007 | Bayer | |
| 2007/0287885 A1* | 12/2007 | Brown | A61M 29/02 600/107 |
| 2007/0293719 A1* | 12/2007 | Scopton | A61B 1/018 600/106 |
| 2007/0293720 A1 | 12/2007 | Bayer | |
| 2008/0021269 A1* | 1/2008 | Tinkham | A61B 1/00098 600/104 |
| 2008/0021274 A1 | 1/2008 | Bayer | |
| 2008/0025413 A1 | 1/2008 | Apostolopoulos | |
| 2008/0036864 A1 | 2/2008 | McCubbrey | |
| 2008/0045797 A1 | 2/2008 | Yasushi | |
| 2008/0058601 A1 | 3/2008 | Fujimori | |
| 2008/0071290 A1 | 3/2008 | Larkin | |
| 2008/0130108 A1 | 6/2008 | Bayer | |
| 2008/0151070 A1 | 6/2008 | Shiozawa | |
| 2008/0161646 A1 | 7/2008 | Gomez | |
| 2008/0163652 A1 | 7/2008 | Shatskin | |
| 2008/0167529 A1 | 7/2008 | Otawara | |
| 2008/0177139 A1 | 7/2008 | Courtney | |
| 2008/0183034 A1 | 7/2008 | Henkin | |
| 2008/0183043 A1 | 7/2008 | Spinnler | |
| 2008/0221388 A1 | 7/2008 | Courtney | |
| 2008/0214890 A1* | 9/2008 | Motai | A61B 1/018 600/107 |
| 2008/0253686 A1 | 10/2008 | Bayer | |
| 2008/0262312 A1 | 10/2008 | Carroll | |
| 2008/0269559 A1* | 10/2008 | Miyamoto | A61B 1/00039 600/116 |
| 2008/0275298 A1* | 11/2008 | Ratnakar | A61B 1/00181 600/109 |
| 2008/0287961 A1* | 11/2008 | Miyamoto | A61B 1/0684 606/127 |
| 2008/0303898 A1 | 12/2008 | Nishimura | |
| 2009/0005643 A1 | 1/2009 | Smith | |
| 2009/0012475 A1* | 1/2009 | Onuki | A61B 1/018 604/164.13 |
| 2009/0023998 A1 | 1/2009 | Ratnakar | |
| 2009/0030275 A1 | 1/2009 | Nicolaou | |
| 2009/0054727 A1* | 2/2009 | Yamaya | G02B 23/2469 600/107 |
| 2009/0054790 A1 | 2/2009 | Czaniera | |
| 2009/0062615 A1 | 3/2009 | Yamaya | |
| 2009/0086017 A1 | 4/2009 | Miyano | |
| 2009/0112060 A1* | 4/2009 | Sugiyama | A61B 1/2736 600/104 |
| 2009/0135245 A1 | 5/2009 | Luo | |
| 2009/0137875 A1 | 5/2009 | Kitagawa | |
| 2009/0143647 A1 | 6/2009 | Banju | |
| 2009/0147076 A1 | 6/2009 | Ertas | |
| 2009/0182194 A1* | 7/2009 | Wood | A61B 1/00098 600/106 |
| 2009/0182917 A1 | 7/2009 | Kim | |
| 2009/0213211 A1 | 8/2009 | Bayer | |
| 2009/0216084 A1 | 8/2009 | Yamane | |
| 2009/0231419 A1 | 9/2009 | Bayer | |
| 2009/0234183 A1 | 9/2009 | Abe | |
| 2009/0253966 A1 | 10/2009 | Ichimura | |
| 2009/0287188 A1 | 11/2009 | Golden | |
| 2009/0287192 A1 | 11/2009 | Vivenzio | |
| 2009/0299144 A1 | 12/2009 | Shigemori | |
| 2010/0010309 A1 | 1/2010 | Kitagawa | |
| 2010/0016673 A1 | 1/2010 | Bandy | |
| 2010/0053312 A1 | 3/2010 | Watanabe | |
| 2010/0069712 A1* | 3/2010 | Yamaya | A61B 1/0125 600/107 |
| 2010/0069713 A1 | 3/2010 | Endo | |
| 2010/0073470 A1 | 3/2010 | Takasaki | |
| 2010/0073948 A1 | 3/2010 | Stein | |
| 2010/0076268 A1 | 3/2010 | Takasugi | |
| 2010/0123950 A1 | 5/2010 | Fujiwara | |
| 2010/0130822 A1 | 5/2010 | Katayama | |
| 2010/0141763 A1 | 6/2010 | Itoh | |
| 2010/0145144 A1* | 6/2010 | Kitano | A61B 1/00098 600/107 |
| 2010/0160729 A1 | 6/2010 | Smith | |
| 2010/0174144 A1 | 7/2010 | Hsu | |
| 2010/0228086 A1* | 9/2010 | Ohki | A61B 1/0125 600/106 |
| 2010/0231702 A1 | 9/2010 | Tsujimura | |
| 2010/0245653 A1 | 9/2010 | Bodor | |
| 2010/0249513 A1 | 9/2010 | Tydlaska | |
| 2010/0256446 A1* | 10/2010 | Raju | A61B 1/018 600/114 |
| 2010/0280322 A1 | 11/2010 | Mizuyoshi | |
| 2010/0296178 A1 | 11/2010 | Genet | |
| 2011/0034769 A1 | 2/2011 | Adair | |
| 2011/0063427 A1 | 3/2011 | Fengler | |
| 2011/0065986 A1* | 3/2011 | Geitz | A61B 1/00133 600/106 |
| 2011/0140003 A1 | 6/2011 | Beck | |
| 2011/0152610 A1* | 6/2011 | Trusty | A61B 1/00101 600/104 |
| 2011/0152616 A1* | 6/2011 | Deal | A61B 1/018 600/114 |
| 2011/0152618 A1* | 6/2011 | Surti | A61B 1/018 600/129 |
| 2011/0160530 A1* | 6/2011 | Ratnakar | A61B 1/00105 600/104 |
| 2011/0160535 A1 | 6/2011 | Bayer | |
| 2011/0169931 A1 | 7/2011 | Pascal | |
| 2011/0184243 A1 | 7/2011 | Wright | |
| 2011/0211267 A1 | 9/2011 | Takato | |
| 2011/0263938 A1 | 10/2011 | Levy | |
| 2011/0282144 A1 | 11/2011 | Gettman | |
| 2011/0292258 A1 | 12/2011 | Adler | |
| 2012/0040305 A1 | 2/2012 | Karazivan | |
| 2012/0050606 A1 | 3/2012 | Debevec | |
| 2012/0053407 A1 | 3/2012 | Levy | |
| 2012/0057251 A1 | 3/2012 | Takato | |
| 2012/0065468 A1 | 3/2012 | Levy | |
| 2012/0076425 A1 | 3/2012 | Brandt | |
| 2012/0078041 A1* | 3/2012 | Kitano | A61B 1/00098 600/107 |
| 2012/0209071 A1 | 8/2012 | Bayer | |
| 2012/0209289 A1 | 8/2012 | Duque | |
| 2012/0212630 A1 | 8/2012 | Pryor | |
| 2012/0220832 A1 | 8/2012 | Nakade | |
| 2012/0224026 A1 | 9/2012 | Bayer | |
| 2012/0229615 A1 | 9/2012 | Kirma | |
| 2012/0232340 A1 | 9/2012 | Levy | |
| 2012/0232343 A1 | 9/2012 | Levy | |
| 2012/0238815 A1* | 9/2012 | Komi | A61B 1/00082 600/114 |
| 2012/0253121 A1 | 10/2012 | Kitano | |
| 2012/0265132 A1* | 10/2012 | Nomura | A61B 1/00098 604/95.04 |
| 2012/0277535 A1 | 11/2012 | Hoshino | |
| 2012/0300999 A1 | 11/2012 | Bayer | |
| 2013/0053646 A1 | 2/2013 | Yamamoto | |
| 2013/0057724 A1 | 3/2013 | Miyahara | |
| 2013/0066297 A1 | 3/2013 | Shtul | |
| 2013/0085329 A1 | 4/2013 | Morrissette | |
| 2013/0109916 A1 | 5/2013 | Levy | |
| 2013/0116506 A1 | 5/2013 | Bayer | |
| 2013/0131447 A1 | 5/2013 | Benning | |
| 2013/0137930 A1 | 5/2013 | Menabde | |
| 2013/0150671 A1 | 6/2013 | Levy | |

(56) References Cited

U.S. PATENT DOCUMENTS

| | | |
|---|---|---|
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0024897 A1* | 1/2014 | Inoue ............... A61B 1/00154 600/115 |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0303553 A1* | 10/2014 | Geitz ............... A61B 1/0057 604/95.04 |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0358088 A1* | 12/2014 | Miyamoto ........... A61B 1/0125 604/164.01 |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0031947 A1* | 1/2015 | Kudo ............... G02B 23/2476 600/104 |
| 2015/0045614 A1 | 2/2015 | Krivopisk |
| 2015/0057500 A1 | 2/2015 | Salman |
| 2015/0087901 A1* | 3/2015 | Shaw ............... A61B 1/00098 600/107 |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0173711 A1* | 6/2015 | Hiraoka ............... A61B 8/4494 600/466 |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0250377 A1* | 9/2015 | Iizuka ............... A61B 1/05 600/103 |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | | |
|---|---|---|---|
| CA | 2812097 | 3/2012 | |
| CA | 2798716 | 6/2013 | |
| CA | 2798729 | 6/2013 | |
| CN | 103348470 | 10/2013 | |
| CN | 103403605 | 11/2013 | |
| CN | 103491854 | 1/2014 | |
| CN | 103702604 | 4/2014 | |
| CN | 103732120 | 4/2014 | |
| CN | 104717916 | 6/2015 | |
| CN | 105246393 | 1/2016 | |
| CN | 105324065 | 2/2016 | |
| CN | 105324066 | 2/2016 | |
| CN | 105338875 | 2/2016 | |
| CN | 105358042 | 2/2016 | |
| CN | 105358043 | 2/2016 | |
| CN | 105377106 | 3/2016 | |
| CN | 105407788 | 3/2016 | |
| DE | 202010016900 | 5/2011 | |
| EP | 1690497 | 8/2006 | |
| EP | 1835844 | 9/2007 | |
| EP | 1968425 | 9/2008 | |
| EP | 1986541 | 11/2008 | |
| EP | 1988813 | 11/2008 | |
| EP | 2023794 | 2/2009 | |
| EP | 2023795 | 2/2009 | |
| EP | 2190341 | 6/2010 | |
| EP | 2211683 | 8/2010 | |
| EP | 2457492 | 5/2012 | |
| EP | 2457493 | 5/2012 | |
| EP | 1988812 | 11/2012 | |
| EP | 2520218 | 11/2012 | |
| EP | 2604175 | 6/2013 | |
| EP | 2618718 | 7/2013 | |
| EP | 2635932 | 9/2013 | |
| EP | 2648602 | 10/2013 | |
| EP | 2649648 | 10/2013 | |
| EP | 2672878 | 12/2013 | |
| EP | 2736400 | 6/2014 | |
| EP | 2744390 | 6/2014 | |
| EP | 2442706 | 11/2014 | |
| EP | 2865322 | 4/2015 | |
| EP | 2908714 | 8/2015 | |
| EP | 2979123 | 2/2016 | |
| EP | 2991537 | 3/2016 | |
| EP | 2994032 | 3/2016 | |
| EP | 2994033 | 3/2016 | |
| EP | 2994034 | 3/2016 | |
| EP | 2996536 | 3/2016 | |
| EP | 2996541 | 3/2016 | |
| EP | 2996542 | 3/2016 | |
| EP | 2996621 | 3/2016 | |
| GB | 12196628 | 3/2015 | |
| JP | H1043129 | 2/1998 | |
| JP | H10239740 | 9/1998 | |
| JP | 10295630 A * | 11/1998 | ......... A61B 1/00098 |
| JP | 11137512 | 5/1999 | |
| JP | 2003305002 A * | 10/2003 | ......... A61B 1/00098 |
| JP | 2005253543 | 9/2005 | |
| JP | 2006025888 | 2/2006 | |
| JP | 2006068109 | 3/2006 | ......... A61B 1/00098 |
| JP | 2010012079 A * | 1/2010 | ......... A61B 1/00098 |
| JP | 2010178766 A | 8/2010 | |
| JP | 2012135432 | 7/2012 | |
| JP | 2013116277 A2 | 6/2013 | |
| JP | 2013123647 | 6/2013 | |
| JP | 2013123648 | 6/2013 | |
| JP | 2013208459 | 10/2013 | |
| JP | 2013215582 | 10/2013 | |
| JP | 2013230383 | 11/2013 | |
| JP | 2013542467 | 11/2013 | |
| JP | 2013544617 | 12/2013 | |
| JP | 2014524303 | 9/2014 | |

(56) References Cited

FOREIGN PATENT DOCUMENTS

| | | |
|---|---|---|
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
International Search Report for PCT/US14/37004, dated Sep. 25, 2014.
International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/58143, dated Jan. 21, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Office Action date Feb. 26, 2016 for U.S. Appl. No. 14/274,323.
Office Action dated Feb. 4, 2016 for U.S. Appl. No. 14/271,234.

* cited by examiner

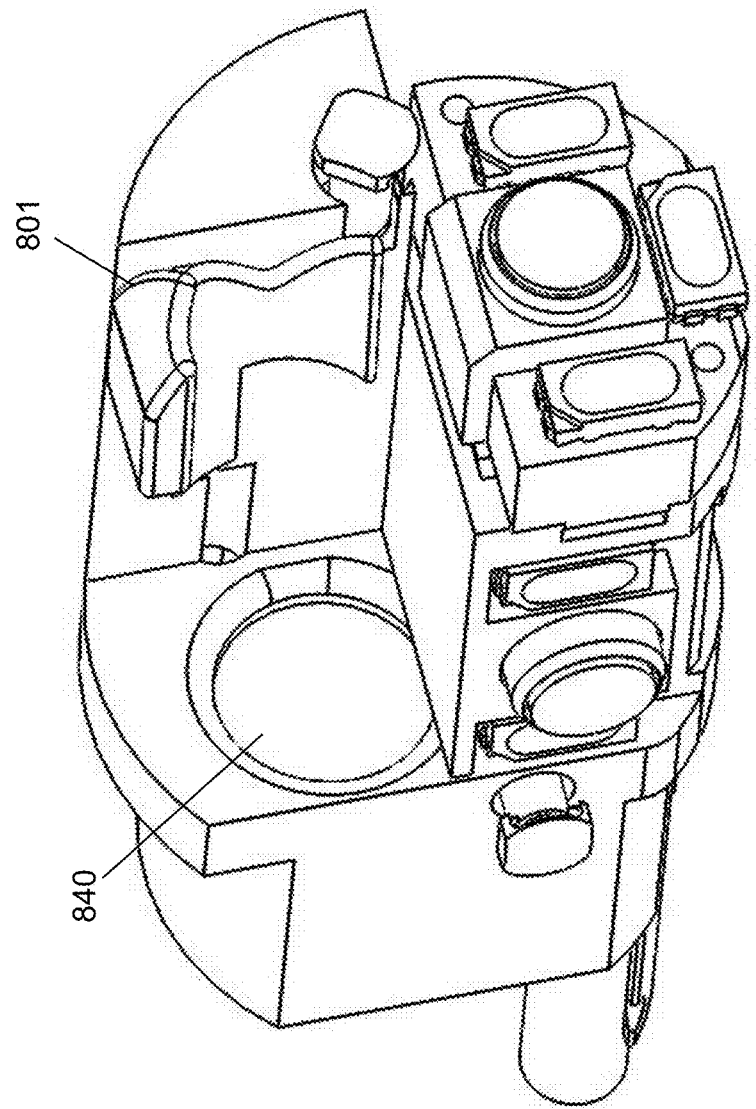

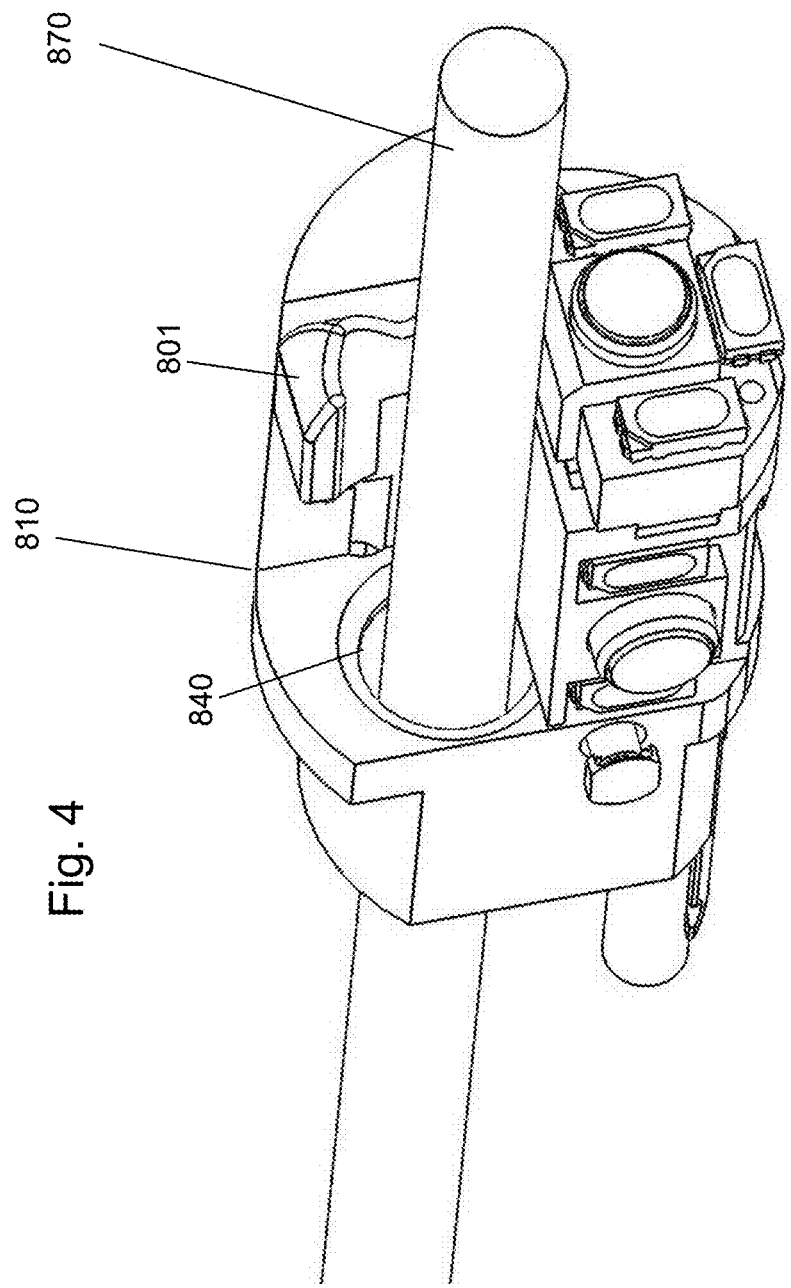

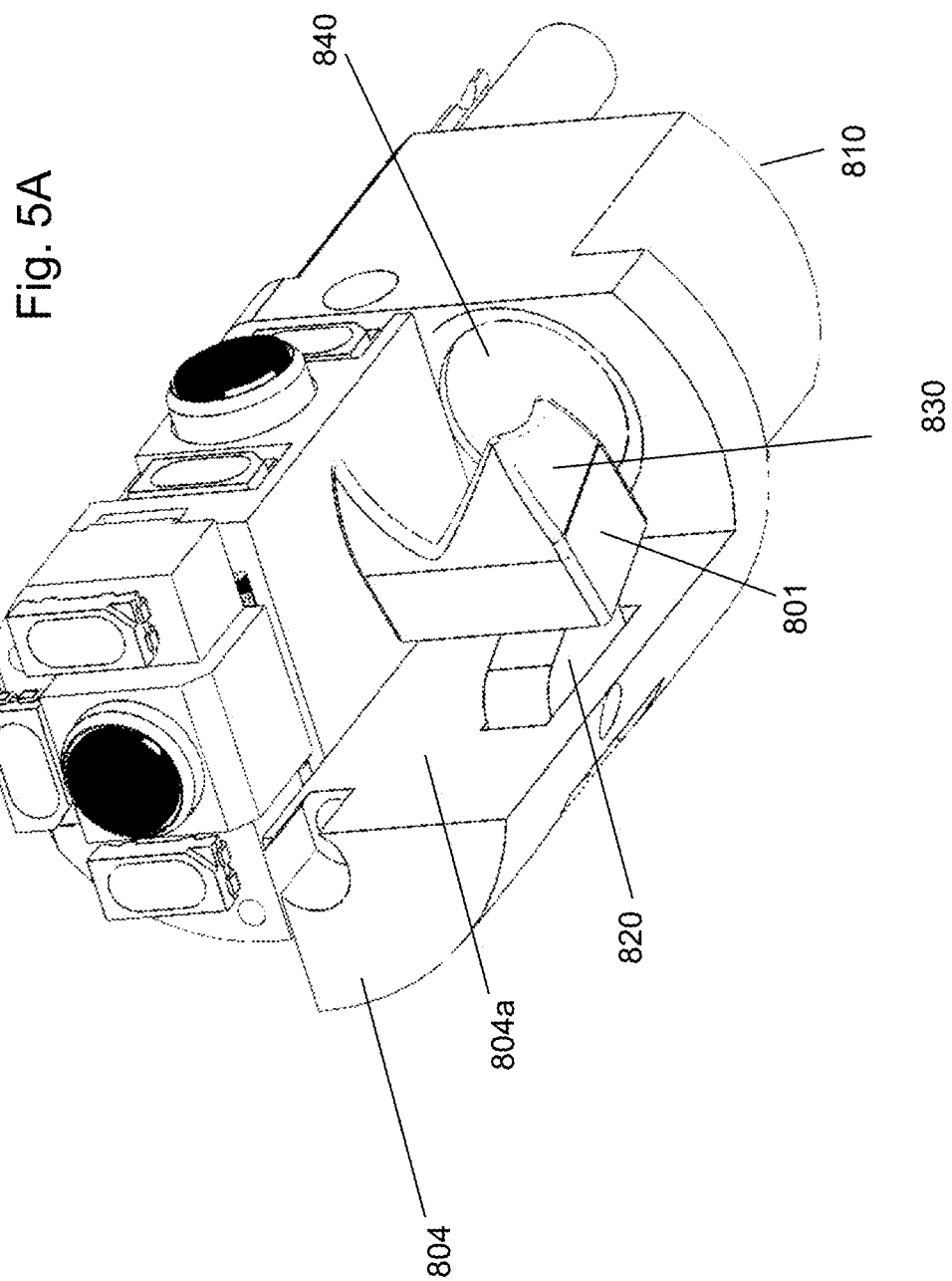

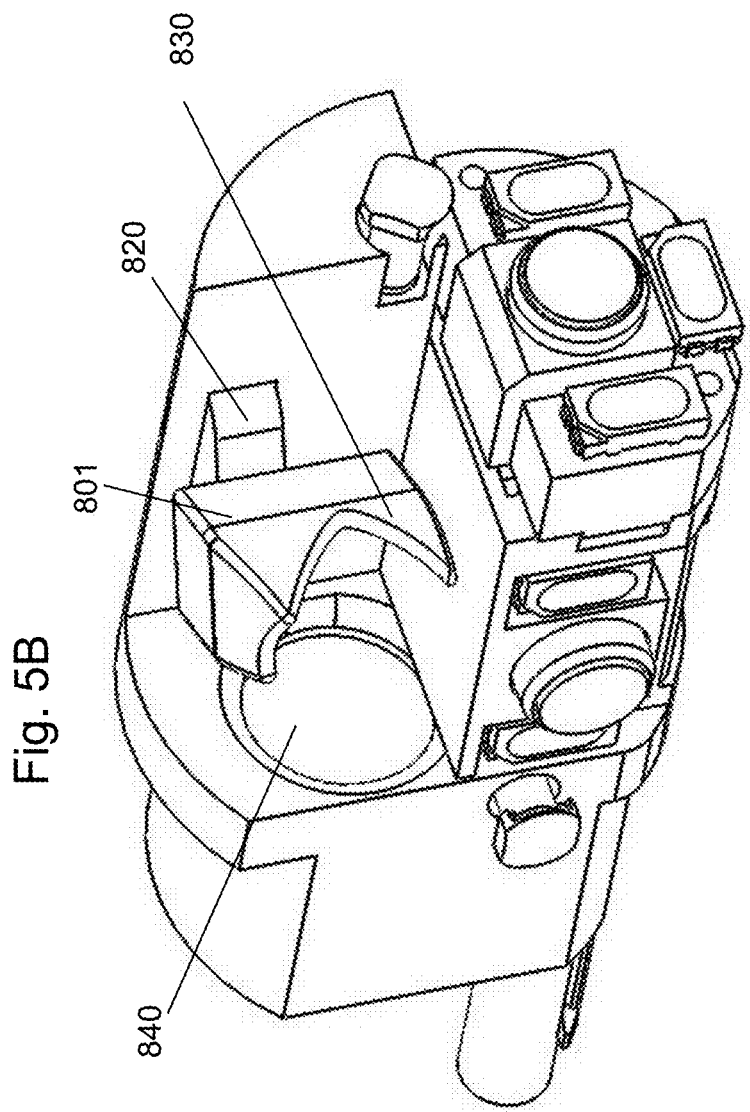

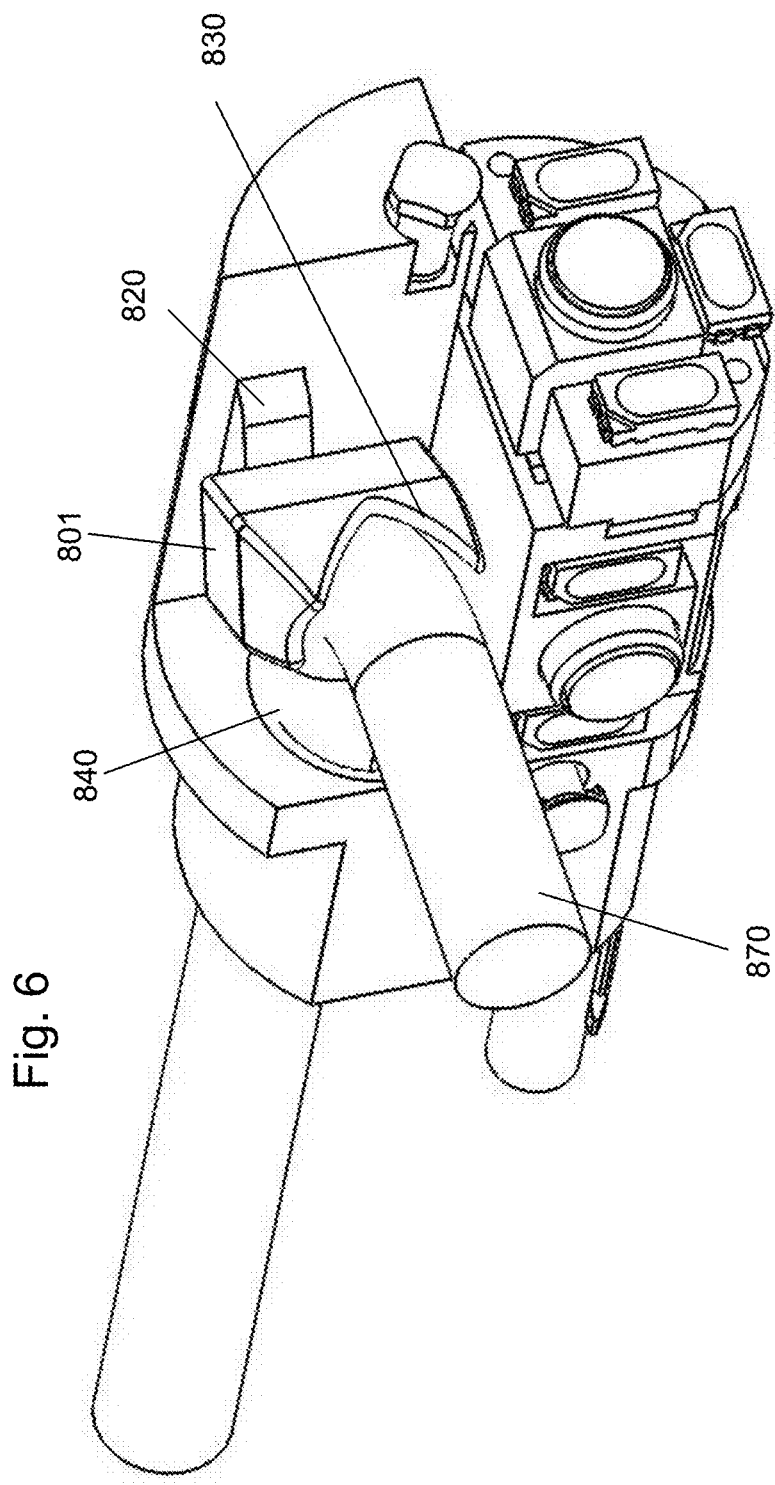

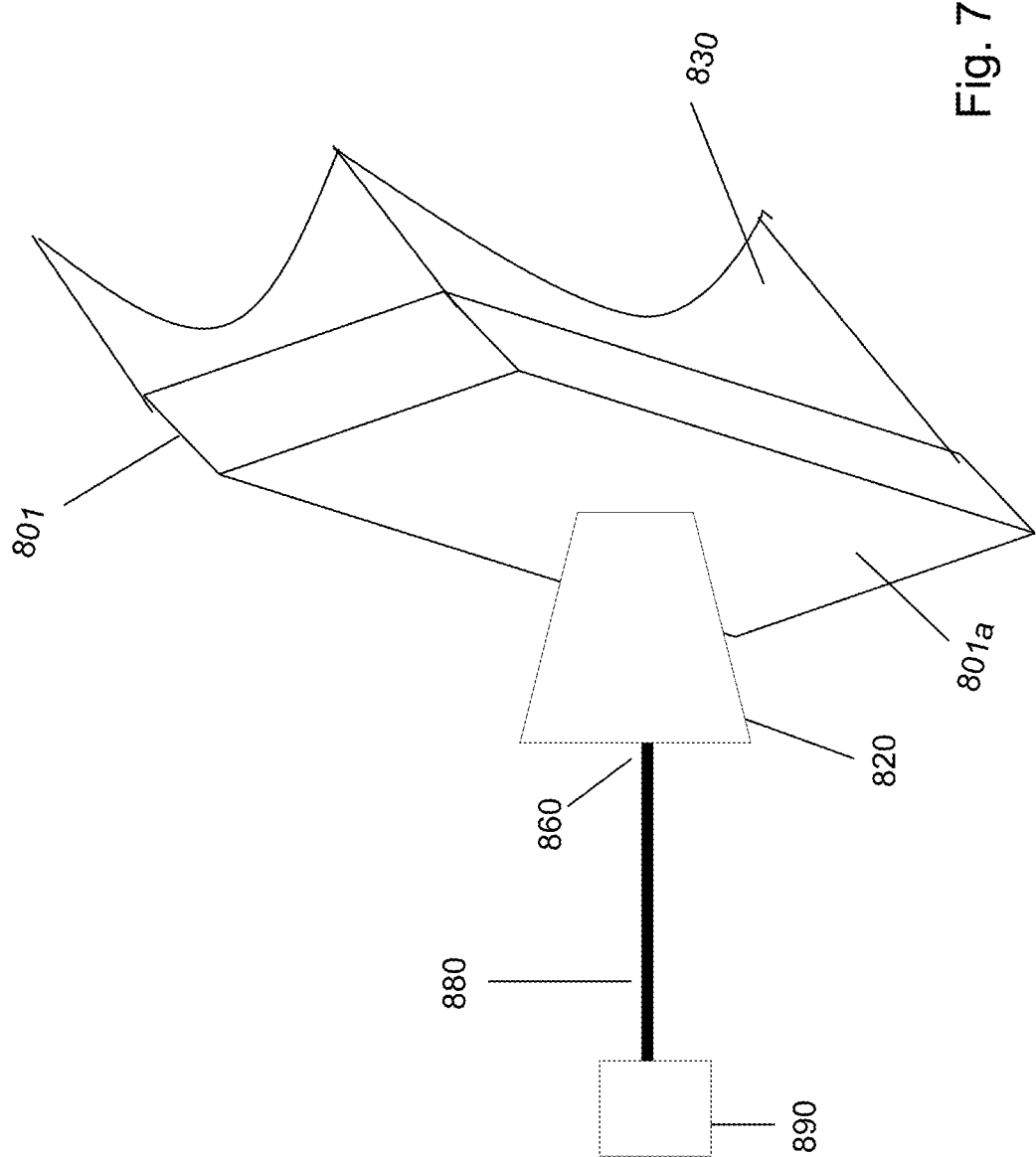

ELEVATOR FOR DIRECTING MEDICAL TOOL

CROSS-REFERENCE

The present specification relies on, for priority, U.S. Provisional Patent Application No. 61/988,084, entitled "Elevator for Directing Medical Tool", and filed on May 2, 2014, herein incorporated by reference in its entirety.

FIELD

The present specification generally relates to multiple viewing element endoscopes and, in particular, describes a multiple viewing element endoscope assembly comprising an elevator mechanism that enables a medical tool to exit from one of a plurality of openings, or working channels, present in the fields of view of at least one of the multiple viewing elements.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having one or more video cameras or fiber optic lens assemblies at its distal end. The shaft is connected to a handle, which sometimes includes an ocular for direct viewing. Viewing is also usually possible via an external screen. Various surgical tools may be inserted through a working channel in the endoscope to perform different surgical procedures.

Endoscopes generally have at least a front viewing element and optionally a side viewing element to view the internal organ, such as the colon, illuminators associated with each viewing element, one or more fluid injectors to clean the lens assembly of the viewing element(s), and a working channel to insert surgical tools, for example, to remove polyps found in the colon. Typically, endoscopes also have fluid injectors ("jet") to clean a body cavity, such as the colon, into which they are inserted. The illuminators commonly used are fiber optics which transmit light, generated remotely, to the endoscope tip section. The use of light-emitting diodes (LEDs) for illumination is also known.

Often surgical tools inserted through a working channel exit from a working channel opening at the front of the distal end of the endoscope tip. The front viewing element allows for the operator to view the tool within the patient's body. In other configurations, surgical tools inserted through a working channel exit from a working channel opening positioned on a side, near the distal end, of the endoscope tip.

Currently available endoscope assemblies do not adequately address the need to exit a surgical tool inserted through the working channel, from either the front opening or one or more side openings located on the distal end of the endoscope tip. Hence there are limitations on the visibility of the body cavity as well as on the ability to reach the cavity and operate on polyps or lesions on the cavity's walls.

U.S. Pat. No. 7,537,561 titled "Endoscope Apparatus" invented by Yamaya et al. describes "an endoscope apparatus comprising: an insertion portion having first and second channels arranged therein and terminating at first and second openings, respectively, at a distal portion of the insertion portion; an observation optical system for capturing an observation image, which is arranged to the insertion portion; a first treatment-tool oscillating base which guides, in a first direction and centering around a first rotating shaft, a first treatment-tool inserted via the first channel arranged to the insertion portion, a range of oscillation of the first treatment-tool by the first treatment-tool oscillating base being set so as to cause a distal end of the first treatment-tool to be selectively positioned inside or outside the observation image; and a second treatment-tool oscillating base which guides, in a second direction which is different from the first direction and centering around a second rotating shaft, a second treatment-tool inserted via the second channel arranged in the insertion portion, the second rotating shaft being positioned closer to the distal portion side of the insertion portion than the first rotating shaft." However, such assemblies with a front-pointing camera with front working channel openings to treat (removing/biopsying) polyps or lesions found on the side walls of the colon need to be refracted and repositioned with their front facing the polyp or lesion. This repositioning of the tip may result in "losing" the polyp/lesion and further effort and time must be invested in re-locating it.

Thus there is a need in the art for an endoscope assembly that allows a medical tool to exit the working channel from the front as well as the side of an endoscope tip, and which may be viewed by corresponding front and side viewing elements.

SUMMARY

The following embodiments and aspects thereof are described and illustrated in conjunction with systems, tools and methods, which are meant to be exemplary and illustrative, not limiting in scope.

The present specification discloses an endoscope assembly, the assembly comprising: at least one front-pointing viewing element on a front end of a distal section of the endoscope assembly; at least one side-looking viewing element on at least one side wall of the distal section of the endoscope assembly; a working channel configured for insertion of a medical tool towards the distal section; and an elevator for directing the medical tool to exit from the working channel in a direction that can be viewed by one of the at least one front-pointing viewing element and the at least one side-looking viewing element.

Optionally, the working channel comprises: a front channel opening on the front end; and a side channel opening on each of the at least one side wall, wherein the front channel opening and the side channel opening allow the medical tool to exit the working channel.

Optionally, the elevator further comprises: a first curvilinear section and a second curvilinear section wherein an edge of the first section is connected to an edge of the second section forming a substantially V-shaped groove for receiving and guiding a medical tool to either the front channel opening or side channel opening; and, a pivot, wherein the pivot enables controlling of the elevator.

The assembly may comprise one side-looking viewing element.

The assembly may comprise two side-looking viewing elements. The side-looking viewing elements may be directed to opposing sides. An optical axis of each side-looking viewing element may be perpendicular to an optical axis of the front-pointing viewing element. An optical axis of each side-looking viewing element may form an obtuse angle with an optical axis of the front-pointing viewing element. An optical axis of each side-looking viewing element may form an acute angle with an optical axis of the front-pointing viewing element.

The present specification also discloses an endoscope assembly having a distal tip section, the assembly comprising: at least one front-pointing viewing element on a front wall of the distal tip section; at least one side-pointing viewing element on at least one side wall of the distal tip section; a working channel configured for insertion of a medical tool into and through the distal tip section, wherein said working channel provides a first exit for said medical tool, said first exit comprising a first opening in the front wall of the distal tip section, and a second exit for said medical tool, said second exit comprising a second opening in the at least one side wall of the distal tip section; a ramp structure, wherein a portion of said ramp structure is positioned proximal to said second exit within said working channel, thereby positioning said second exit between the first exit and the portion of the ramp structure, wherein said ramp structure is coupled to an internal wall of the distal tip section via a pivot and wherein a position of the ramp structure may be modified to regulate a direction of exit of the medical tool; and a control system coupled to said pivot, wherein said control system is configured to modify a position of said ramp structure to regulate the direction of exit of the said medical device.

The ramp may be adapted to be positioned in at least two different angles relative to the internal wall of the distal tip section.

Optionally, the ramp structure comprises partially raised walls on side edges which are configured to hold and guide an elongated surface of the medical tool.

The pivot may comprise at least one of pivot hinge joint, pivot ball and socket joint, pivot pin and hole joint.

Optionally, the control system comprises a control wire coupled to the pivot at a first end and to a control knob positioned on a handle section of the endoscope assembly at a second end.

The control system may comprise an electronic controller.

When said pivot is in a first position, the ramp structure may be positioned to enable the medical tool to exit from the first exit of the distal tip section. Additionally, when said pivot direction is in a first position, said medical tool may exit from the front wall of the distal tip section at an angle of substantially zero degrees relative to the long dimension towards the front portion of the endoscope device.

When said pivot direction is in a second position, the ramp structure may be configured to receive and bend the medical tool to enable it to exit from the second exit. Additionally, when said pivot direction is in a second position, said medical tool may exit from the second exit at an angle of approximately 90 degrees relative to the long dimension towards the front portion of the endoscope device.

Optionally, said ramp structure further comprises a first curvilinear section and a second curvilinear section wherein an edge of the first section is connected to an edge of the second section forming a groove for receiving and guiding a medical tool to either the first exit or the second exit.

The present specification also discloses an endoscope assembly having a distal tip section, the assembly comprising: at least one front-pointing viewing element on a front wall of the distal tip section; at least one side-pointing viewing element on a side wall of the distal tip section; a working channel configured for insertion of a medical tool into and through the distal tip section, wherein said working channel provides a first exit for said medical tool, said first exit comprising a first opening in the front wall of the distal tip section, and a second exit for said medical tool, said second exit comprising a second opening in the at least one side wall of the distal tip section, wherein said first exit and second exit are separated by a distance of 7 mm to 11 mm; a ramp structure, wherein said ramp structure is coupled to an internal wall of the distal tip section via a pivot, wherein a position of the ramp structure may be modified to regulate a direction of exit of the medical tool, and wherein said pivot is positioned at least 0.3 mm proximal to the second exit within said working channel, thereby placing said second exit between the first exit and the pivot; and a control system configured to modify a position of said ramp structure to regulate the direction of exit of the said medical device, wherein said control system comprises a control wire coupled to the pivot at a first end and to a control knob positioned on a handle section of the endoscope assembly at a second end.

The ramp may be adapted to be positioned in at least two different angles relative to the internal wall of the distal tip section.

Optionally, the ramp structure comprises partially raised walls on side edges which are configured to hold and guide an elongated surface of the medical tool.

When said pivot is in a first position, the ramp structure may be positioned to enable the medical tool to exit from the first exit of the distal tip section. Additionally, when said pivot direction is in a first position, said medical tool may exit from the front wall of the distal tip section parallel to the long dimension towards the front portion of the endoscope device.

When said pivot direction is in a second position, the ramp structure may be configured to receive and bend the medical tool to enable it to exit from the second exit. Additionally, when said pivot direction is in a second position, said medical tool may exit from the second exit at an angle of approximately 90 degrees relative to a long dimension towards the front portion of the endoscope device.

Optionally, said ramp structure further comprises a first curvilinear section and a second curvilinear section wherein an edge of the first section is connected to an edge of the second section forming a groove for receiving and guiding a medical tool to either the first exit or the second exit.

The present specification also discloses an endoscope assembly having a distal tip section, the assembly comprising: at least one front-pointing viewing element on a front wall of the distal tip section; at least one side-pointing viewing element on a side wall of the distal tip section; a working channel configured for insertion of a medical tool into and through the distal tip section, wherein said working channel provides a first exit for said medical tool, said first exit comprising a first opening in the front wall of the distal tip section, and a second exit for said medical tool, said second exit comprising a second opening in the at least one side wall of the distal tip section, wherein said first exit and second exit are separated by a distance of 7 mm to 11 mm; a ramp structure having a distal end and a proximal end with a pivot point, wherein said ramp structure is coupled to an internal wall of the distal tip section via the pivot point, wherein a position of the ramp structure may be modified to regulate a direction of exit of the medical tool, and wherein said distal end of the ramp structure is positioned at least 0.3 mm proximal to the second exit within said working channel, thereby placing said second exit between the first exit and the distal end of the ramp structure; and a control system configured to modify a position of said ramp structure to regulate the direction of exit of the said medical device, wherein said control system comprises a control wire coupled to the pivot at a first end and to a control knob positioned on a handle section of the endoscope assembly at a second end.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 3B shows a another view of the tip section according to some embodiments;

FIG. 4 illustrates a medical tool guided by a ramp to exit a front channel opening in the tip section according to some embodiments;

FIG. 5A illustrates an alternative position of a ramp, in accordance with an embodiment;

FIG. 5B illustrates an another view of an alternative position of a ramp shown in FIG. 5a, in accordance with an embodiment;

FIG. 6 illustrates a medical tool guided by a ramp to exit a side channel opening in the tip section according to some embodiments; and, FIG. 7 illustrates a control system to regulate the position of ramp/elevator in accordance with an embodiment.

DETAILED DESCRIPTION OF THE INVENTION

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
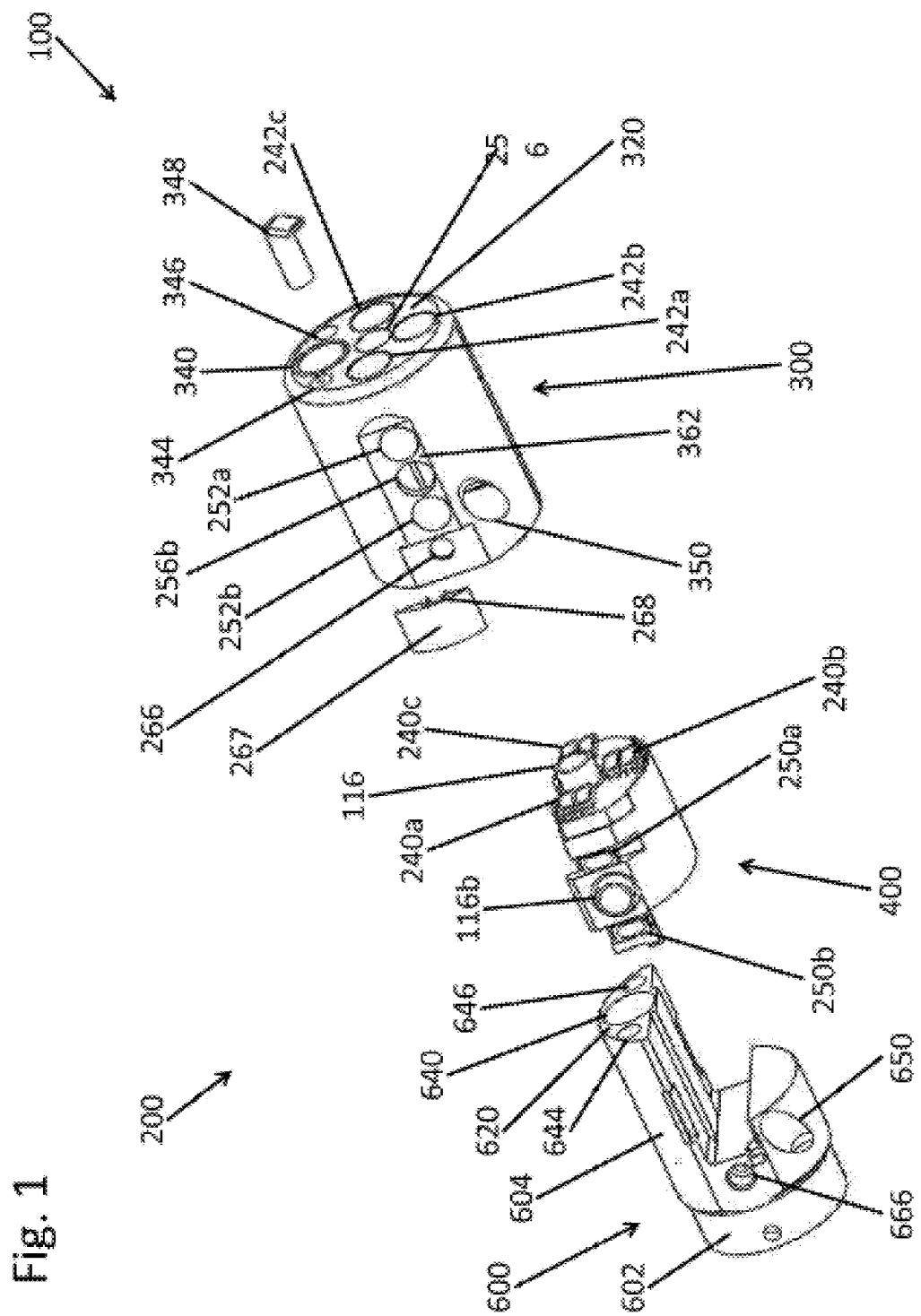
FIG. 1 shows an exploded view of a tip section of an endoscope assembly according to some embodiments.

Reference is now made to FIG. 1, which shows an exploded view of a tip section 200 of an endoscope assembly 100. It is noted that the term "endoscope" as mentioned to herein may refer particularly to a duodenoscope or colonoscope, according to some embodiments, but is not limited only to duodenoscopes or colonoscopes. The term "endoscope" may refer to any instrument used to capture images of, and visualize, the interior of a hollow organ or cavity of the body.

As shown in FIG. 1, the tip section 200 is turnable by way of flexible shaft (not shown), which may also be referred to as a bending section, for example a vertebra mechanism. According to an embodiment, tip section 200 of an endoscope includes a tip cover 300, an electronic circuit board assembly 400 and a fluid channeling component 600.

The electronic circuit board assembly 400 is configured to carry a front pointing viewing element 116 and two side looking viewing elements such as viewing element 116b on one side and another viewing element on the side opposite to one carrying the viewing element 116b, which may be similar to front pointing viewing element 116 and may include a Charge Coupled Device (CCD) or a Complementary Metal Oxide Semiconductor (CMOS) image sensor.

The electronic circuit board assembly 400 is also configured to carry front illuminators 240a, 240b, 240c, which are associated with front pointing viewing element 116, and are positioned to illuminate its field of view. In addition, the electronic circuit board assembly 400 is configured to carry side illuminators 250a and 250b, which are associated with side looking viewing element 116b, and are positioned to illuminate its field of view. Electronic circuit board assembly 400 is also configured to carry side illuminators associated with side looking viewing element opposing side looking viewing element (116b), which may be similar to side illuminators 250a and 250b.

In an embodiment, the front illuminators 240a, 240b, 240c and side illuminators 250a and 250b are discrete illuminators and include a light-emitting diode (LED), which may be a white light LED, an infrared light LED, a near infrared light LED, an ultraviolet light LED or any other LED. The term "discrete", concerning discrete illuminator, refers to an illumination source, which generates light internally—in contrast to a non-discrete illuminator, which may be, for example, a fiber optic merely transmitting light generated remotely.

Figure 2A:
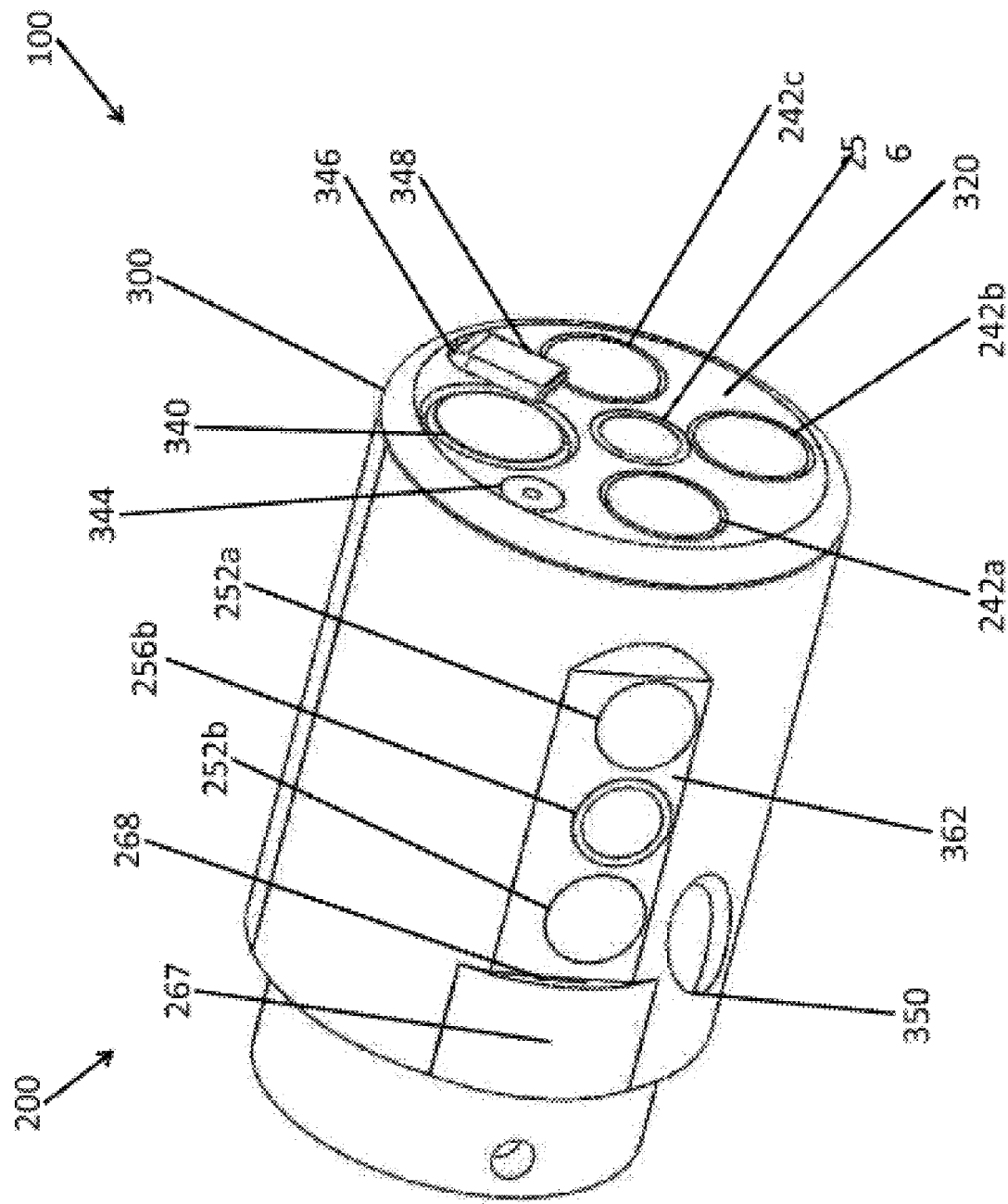
FIG. 2A shows an alternate view of a tip section of an endoscope assembly according to some embodiments.
Figure 2B:
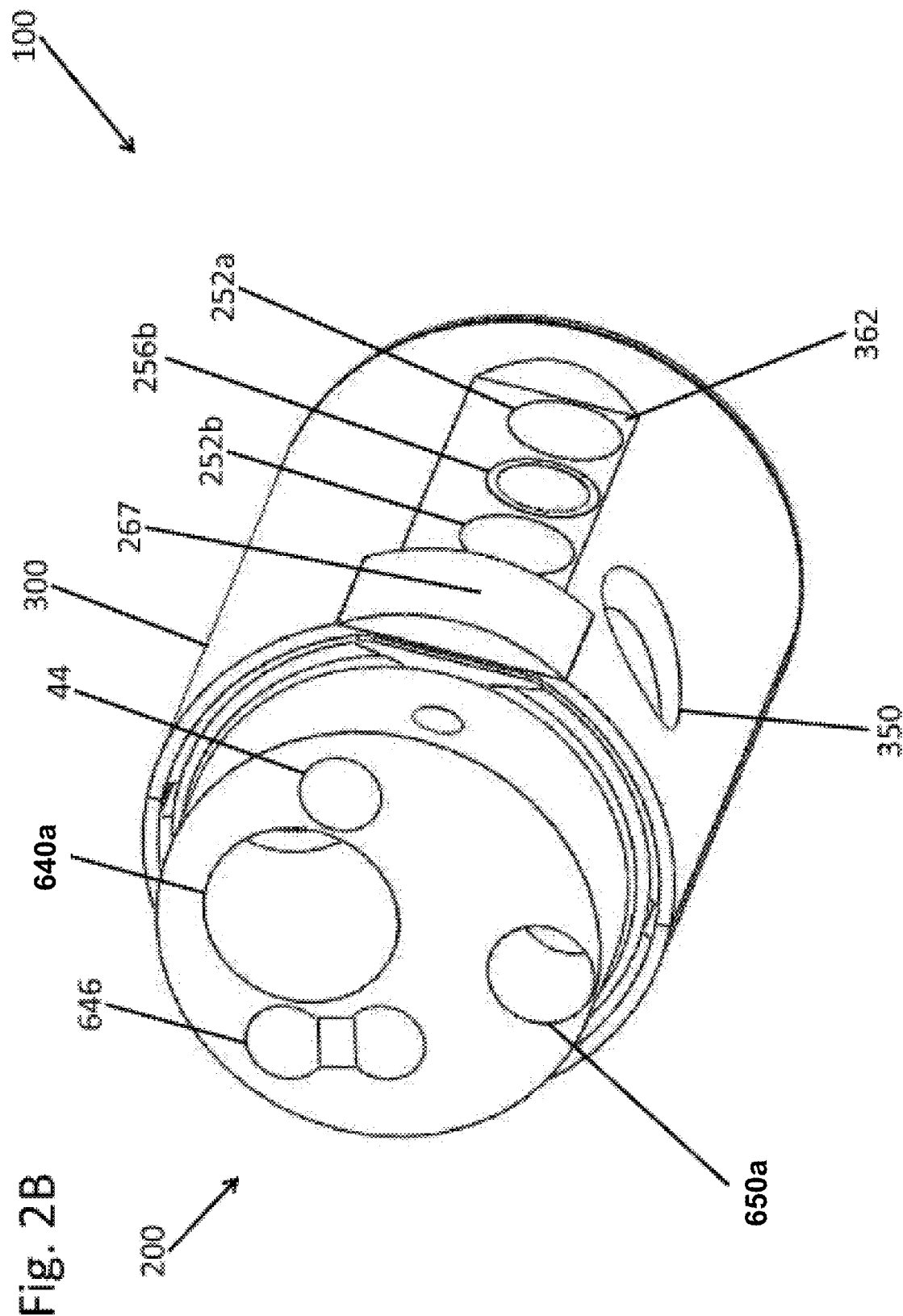
FIG. 2B shows another view of a tip section of an endoscope assembly according to some embodiments.

Reference is now made to FIG. 1 along with FIGS. 2A and 2B, which shows alternate views of the tip section 200. According to some embodiments, fluid channeling component 600 includes a proximal fluid channeling section 602 (or base) which has an cylindrical shape and a unitary distal channeling section 604 (or elongated housing). Distal fluid channeling section 604 partially continues the cylindrical shape of proximal fluid channeling section 602 and has a shape of a partial cylinder (optionally elongated partial cylinder).

In an embodiment, the fluid channeling component 600 comprises a front working channel 640 having an entry point 640a (Refer FIG. 2B) and a side working channel 650 having an entry point 650a (Refer FIG. 2B). The entry points 640a and 650a are located on the rear side of the fluid channeling component 600 of the tip section 200 as illustrated in FIG. 2B.

The tip cover 300 is configured to fit over the inner modules of tip section 200 including electronic circuit board assembly 400 and fluid channeling component 600 and to provide protection to the internal components housed within the inner modules. The opening 340 on the tip cover 300 provides an exit point for the front working channel 640 and the opening 350 on the tip cover 300 provides an exit point for the side working channel 650. Further, the tip cover 300 includes a front panel 320 having a front optical assembly 256, of front looking viewing element 116. Front optical assembly 256 includes a plurality of lenses, static or movable, which provide a field of view of 90 degrees or more, 120 degrees or more or up to essentially 180 degrees.

Optical axis of front looking viewing element 116 is essentially directed along the long dimension of the endoscope. However, in embodiments, since front looking viewing element 116 is a wide angle camera, its field of view may include viewing directions at large angles to its optical axis. Additionally, in an embodiment, the front panel 320 includes optical windows 242a, 242b, and 242c which cover the illuminators 240a, 240b and 240c, respectively. It should be noted that number of illumination sources used for illumination of the field of view might vary.

In addition, the front panel 320 includes a working channel opening 340 of a working channel 640, which is further discussed below.

In another configuration, a jet channel opening 344 of jet channel 644 is located on front panel 320 of tip cover 300. Jet channel 644 is configured to provide high-pressure jet of fluid such as water or saline for cleaning the walls of the body cavity in an embodiment.

Also located on front panel 320 of tip cover 300 is injector opening 346 of injector channel 646 having a nozzle 348 aimed at front optical assembly 256. Injector channel 646 is configured for injecting fluid (liquid and/or gas) to wash contaminants such as blood, feces and other debris from front optical assembly 256 of front looking viewing element 116. Optionally, injector channel 646 may be configured for cleaning front optical assembly 256 and one, two, or all of optical windows 242a, 242b, and 242c. Visible on sidewall 362 of tip cover 300 is side optical assembly 256b for side looking viewing element 116b, which may be similar to front optical assembly 256 and optical windows 252a and 252b of illuminators 250a and 250b. Also on sidewall 362 of tip cover 300, on the opposing side to side optical assembly 256b, is an optical assembly (not shown) for side looking viewing element, and optical windows of the illuminators corresponding to side looking viewing element. In an embodiment, the optical axis of side looking viewing element 116b is directed perpendicular to the long dimension of the endoscope. However, in embodiments, since side looking viewing element 116b is a wide angle camera, its field of view includes viewing directions at large angles to its optical axis. In accordance with some embodiments, the side looking viewing element 116b has a field of view of 90 degrees or more, 120 degrees or more or up to essentially 180 degrees.

In embodiments, optical axis of each side-looking viewing element (116b and the opposing viewing element) is perpendicular to optical axis of front-pointing viewing element 116. In alternative embodiments, optical axis of each side-looking viewing element forms an obtuse angle with optical axis of front-pointing viewing element 116. In other embodiments, optical axis of each side-looking viewing element forms an acute angle with optical axis of front-pointing viewing element 116.

In addition, in an embodiment, the side injector opening 266 of side injector channel 666 is located at distal end of sidewall 362. A nozzle cover 267 is configured to fit side injector opening 266.

Additionally, in an embodiment, nozzle cover 267 includes a nozzle 268 which is aimed at side optical assembly 256b and is configured to inject fluid to wash contaminants such as blood, feces, and other debris from side optical assembly 256b of side looking viewing element 116b. The fluid may include gas that is used for inflating a body cavity. Optionally, nozzle 268 is configured to clean both side optical assembly 256b and optical windows 252a and/or 252b.

According to some embodiments, side injector channel 666 is configured to supply fluids to clean any of the tip elements (such as any optical assembly, windows, illuminators, and other elements).

Although the tip section 200 is presented herein showing one side thereof, it is noted that according to some embodiments, the opposing side may include elements similar to the side elements described herein (for example, side looking viewing element, side optical assembly, injector(s), nozzle(s), illuminator(s), window(s), opening(s) and other elements).

It is noted that according to some embodiments, tip section 200 includes more than one side looking viewing elements. In this case, the side looking viewing elements are installed such that their field of views are substantially opposing. Front-pointing viewing element 116 is able to detect objects of interest (such as a polyp or another pathology) which are directly in its field of view, while side looking viewing elements are configured to detect additional objects of interest that are normally hidden from front-pointing viewing element 116. Once an object of interest is detected, endoscope operator can insert a surgical tool and remove, treat and/or extract a sample of the polyp or its entirety for biopsy.

In some cases, objects of interest may only be visible through side looking viewing elements such as 116b. In this case, it is beneficial for the endoscope's operator to be able to use surgical tools, which can access the object of interest and perform surgical operations while the object of interest is visible by such side looking viewing elements.

According to some embodiments, fluid channeling component 600 is configured as a separate component from electronic circuit board assembly 400. This configuration is adapted to separate the fluid channels and working channel 640, which are located in fluid channeling component 600 from the sensitive electronic and optical parts that are present in electronic circuit board assembly 400.

In an embodiment, the tip cover 300 of the tip section 200 includes a side working channel opening 350 for the side working channel 650 as mentioned earlier. Side working channel opening 350 is configured to improve the performance of the endoscope (particularly, the colonoscope). Typically colonoscopes have only one working channel opening such as the opening 340 provided for front working channel 640, which opens at the front distal section of the colonoscope. Such front working channel is adapted for insertion of a surgical tool. The physician is required to perform all necessary medical procedures, such as biopsy, polyp removal and other procedures, through the front opening.

In addition, for treating (removing/biopsying) polyps or lesions found on the side walls of the colon, tip sections that only have one or more front working channels need to be retracted and repositioned with their front facing the polyp or lesion. This repositioning of the tip may result in "losing" the polyp/lesion and further effort and time must be invested in relocating it. However, the configuration shown in FIG. 1 describes an endoscope (such as colonoscope) having a front viewing element and one or more side viewing elements which comprises, in addition to the front working channel opening 340, a side working channel opening 350. The front working channel 640 is configured for the insertion of medical tools that can exit from front working channel opening 340. Similarly the side working channel 650 is configured such that the medical tools inserted through it can exit from the side working channel opening 350.

While some objects of interest may be visible and/or accessible via the endoscope's front panel 320 (FIG. 1), some objects of interest may be more visible via side looking viewing element 116b and/or accessible via endoscope side working channel opening 350 of the side working channel 650. Allowing an exit from side working channel opening 350 enables medical procedures to be performed from (or in proximity to) the side of tip section 200, while at the same time viewing the procedure by side looking viewing element 116b. This substantially increases the performance and accessibility of the endoscope. In an embodiment, the tip section of the endoscope assembly 200 comprises another working channel opening on the side opposite to that shown in FIG. 2A, which allows the physicians to operate on polyps or lesions detected by side viewing element present on the side opposite to side having the sidewall 362.

As discussed in the configurations shown in FIGS. 1, 2A and 2B, the endoscope assemblies described here comprise multiple separate working channels to provide operational access to both the front portion and side portions of the device. It includes separate entry and exit points for the front working channel 640 and the side working channel 650.

The present specification describes a novel system for providing operational access to both the front portion and side portion of device from a single working channel. In an embodiment, the present specification describes a system wherein the medical tools inserted through a single working channel can be diverted to exit through both the front opening and side wall openings at multiple angles relative to the long dimension of the device. In an embodiment, the present specification describes a system wherein the exit angle of the medical tool is regulated with the help of an elevator/ramp mechanism which in an embodiment, is controlled by the physician.

Figure 3A:
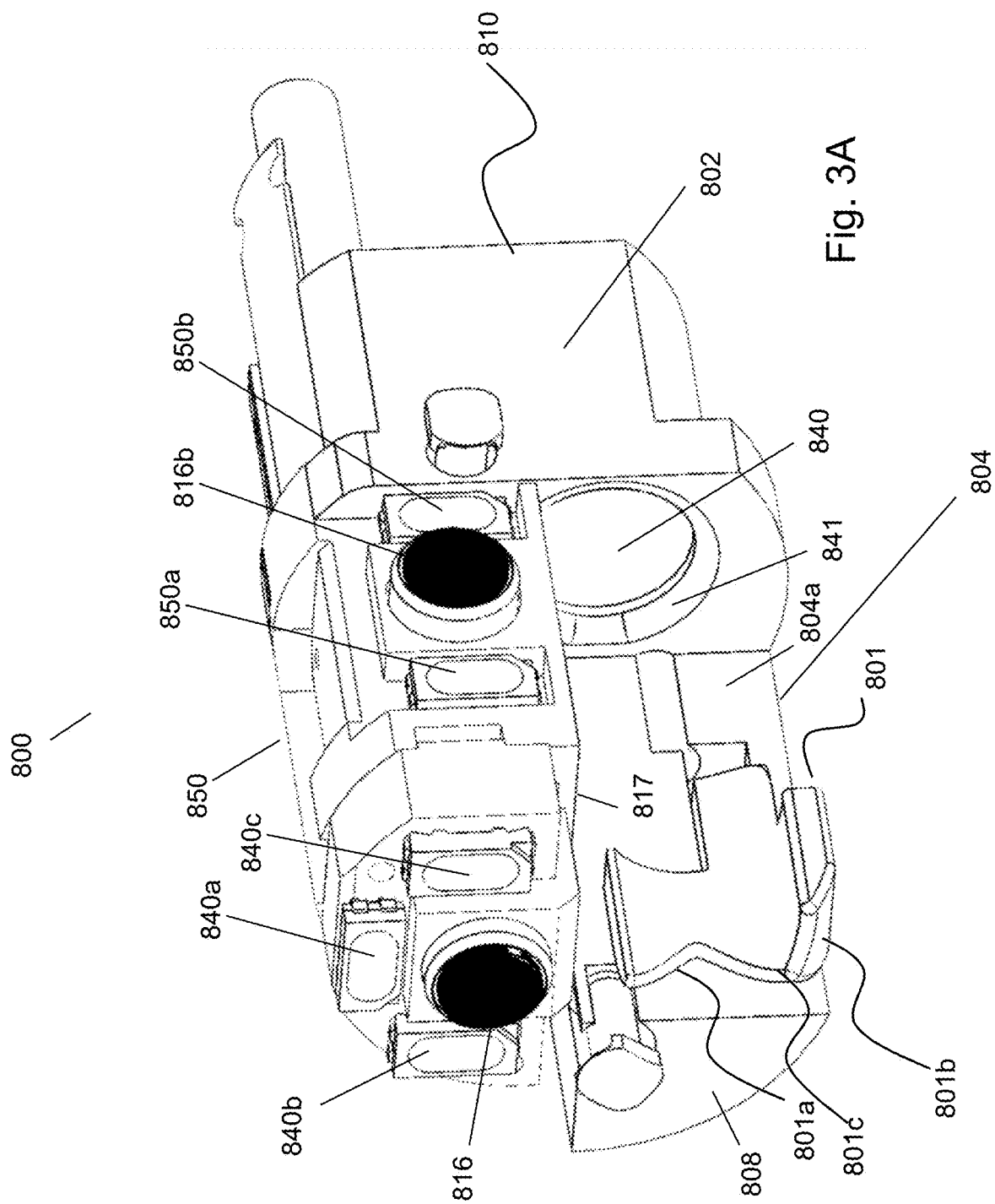
FIG. 3A illustrates a cross-sectional view of a tip section of an endoscope assembly according to some embodiments.

Reference is now made to FIG. 3A and FIG. 3B which illustrate a cross-sectional view of the tip section 800 of an endoscope device in accordance with an embodiment of the present specification. In an embodiment, the tip section 800 comprises a fluid channeling component 810 that includes a proximal fluid channeling section 802 (or base) and a distal channeling section 804 (or elongated housing). In an embodiment, the distal fluid channeling section 804 partially continues the shape of proximal fluid channeling section 802 and in an embodiment has a shape of a truncated partial cylinder.

In an embodiment of the present specification, the tip section 800 comprises an electronic circuit board 850 coupled to the fluid channeling component 810. The electronic circuit board assembly 850 is configured to carry a front pointing viewing element 816 and two side looking viewing elements such as viewing element 816b on one side and another viewing element on the side opposite to one carrying the viewing element 816b, which may be similar to front pointing viewing element 816 and may include a Charge Coupled Device (CCD) or a Complementary Metal Oxide Semiconductor (CMOS) image sensor.

The electronic circuit board assembly 850 is also configured to carry front illuminators 840a, 840b, 840c, which are associated with front pointing viewing element 816, and are positioned to illuminate its field of view. In addition, the electronic circuit board assembly 850 is configured to carry side illuminators 850a and 850b, which are associated with side looking viewing element 816b, and are positioned to illuminate its field of view. Electronic circuit board assembly 850 is also configured to carry side illuminators associated with side looking viewing element opposing side looking viewing element (816b), which may be similar to side illuminators 850a and 850b.

In an embodiment, the front illuminators 840a, 840b, 840c and side illuminators 850a and 850b are discrete illuminators and include a light-emitting diode (LED), which may be a white light LED, an infrared light LED, a near infrared light LED, an ultraviolet light LED or any other LED. The term "discrete", concerning discrete illuminator, refers to an illumination source, which generates light internally—in contrast to a non-discrete illuminator, which may be, for example, a fiber optic merely transmitting light generated remotely.

According to some embodiments, the proximal fluid channeling section 802 comprises a working channel 840. Medical tools inserted in the working channel 840 from the rear portion (facing the physician) of the fluid channeling component 810, can exit from opening 841 located within the fluid channeling section 802. As the medical tool exits from opening 841, in an embodiment, the medical tool is subsequently allowed to either travel in a straight line direction or the direction of medical tool is diverted with help of an elevator/ramp structure 801.

In an embodiment, the ramp structure 801 comprises a first section 801a and a second section 801b wherein an edge of the first section 801a is connected to an edge of the second section 801b forming a substantially angled structure, or V-shaped groove, 801c for receiving and guiding a medical tool to the appropriate working channel opening. In embodiments, the shape of the groove may not be limited to a V-shape; and any other shape such as a hyperbola, square, or any other suitable shape, may be used to handle and guide the medical tool.

In an embodiment, the first section 801a of the ramp structure 801 comprises a planar structure that is positioned substantially parallel to the inside wall 804a of the fluid channeling component 810 and defines a plane that intersects with the plane defining the base 817 of the electronic circuit board 850 at a right angle. In another embodiment, the plane defined by the first section 801a bisects the base 817 of the electronic circuit board 850 at a right angle.

In an embodiment, the second section 801b comprises a planar structure that is substantially parallel to the plane defined by the base 817 of the electronic circuit board 850 and is positioned at a right angle to the first section 801a and inside wall 804a of the fluid channeling component 810.

One of ordinary skill in the art would appreciate that the above described configuration and positioning of the ramp structure 801 only defines its initial configuration in an embodiment and the position and relative angular orientation of ramp 801 changes as the ramp is moved with the help of a pivot to regulate the direction of medical tool which is discussed in subsequent sections of the specification.

In an embodiment, the first section 801a and second section 801b have substantially curvilinear structures. In an embodiment, the ramp structure 801 is pivotally connected to the internal side 804a of the fluid channeling component 810. In an embodiment, a pivot is connected to ramp 801 such that by controlling the position of pivot, one can control the angle at which ramp 801 aligns with inner wall 804a of fluid channeling component 810, which in turn controls the direction in which the medical tool exits the endoscope assembly.

In an embodiment, the system is configured such that ramp structure 801 can be positioned among seven different positions to provide seven different exit directions to the medical tool inserted through the working channel 840. In these seven positions, the ramp is inclined at an angle of 0 degree, 15 degree, 30 degree, 45 degree, 60 degree, 75 degree and 90 degree to the long dimension of the endoscope, where each degree covers a range of +/−five degrees. Accordingly the medical tool exits at angles of zero degree, 15 degree, 30 degree, 45 degree, 60 degree, 75 degree and 90 degree to the long dimension of the endoscope in these respective positions.

In an embodiment, slightly raised walls on the side edges of ramp 801 are configured to hold and guide the elongated surface of the medical tool passing over it in position during an endoscopic procedure. In an embodiment, the ramp 801 is positioned between front section 808 of the distal channeling section 804 and the opening 841 of the working channel 840, such that changing the position of the ramp guides the medical tool to exit either through the front panel or through an exit in a sidewall of the endoscope device. In embodiments, the ramp position can be regulated to enable the medical tool to exit at multiple angles from both the front panel and sidewall of the device. In an embodiment, the equipment manufacturer provides openings for exit of working channel on the front panel and on sidewalls of the endoscope device and the ramp position is allowed to shift between a predefined positions such that the medical tool can exit from these existing openings on the device.

In embodiments, front-pointing viewing element 816, aided by illuminators 840a, 840b and 840c, is configured to provide a view of the medical tool exiting through a front channel opening located on a front portion of the distal tip of the endoscope. Similarly, in embodiments, side-looking viewing element 816b, aided by illuminators 850a and 850b, is configured to provide a view of the medical tool when it exits through a side wall of the endoscope device.

In FIG. 3A, the pivot is in a first position such that the first section 801a of ramp 801 is in a plane parallel to the inner wall 804a of fluid channeling component 810. In an embodiment, a medical tool inserted through working channel 840 exits at zero degrees relative to the long dimension towards the front portion of the device (illustrated in FIG. 4) through a front channel opening provided on the front panel of the device. In an another embodiment, the pivot is turned to raise the ramp such that it guides the medical tool passing over in a way that the said medical tool bends and exits from one of the side channel openings provided on the device. In an embodiment, the position of pivot is controlled such that the medical tool bends at 90 degrees (illustrated and described in context of FIGS. 5a, b, and 6) or less when it exits a side channel opening provided on a side wall of the endoscope device. In embodiments, the pivot coupled to the ramp 801 is controlled by adding a control component such as a lever to a handle of endoscope assembly. In an embodiment, the lever is placed between knobs on the handle and the handle's body.

One of ordinary skill in the art would appreciate that FIG. 3A describes a tip section of the endoscope assembly without the external tip cover. In an embodiment, the tip section is covered by a tip cover such as the tip cover 300 described for endoscope assembly of FIG. 1. In an embodiment, the tip cover of the endoscope assembly described in FIG. 3A has at least one side channel opening positioned at an appropriate position to provide an exit to the medical tool which is maneuvered with the help of ramp structure 801 towards a side wall of the endoscope tip section (as described in the FIG. 6). One of ordinary skill in the art would appreciate that the side working channel opening on such tip cover can be positioned at any convenient location as per the system requirement. In an embodiment, the side working channel opening is located closer to the front portion of the tip section compared to the position of viewing element 816b on the side wall. In another embodiment, the side working channel opening and the viewing element 816b are located at same horizontal distance from the front portion of the distal tip. In an embodiment, the viewing element 816b is located closer to the front portion of the tip section compared to the position of side working channel opening.

In an embodiment, in order to ensure that the medical tools operated through the side working channel are viewed properly, the side working channel opening is positioned such that the medical tools operated through the side working channel opening are within the field of view of a side viewing element such as the viewing element 816b on the sidewall of endoscope.

In an embodiment, the side working channel opening is positioned on the circumference of the endoscope at a distance of 7 to 11 millimeters, preferably 8.5 mm to 9.5 mm, and more preferably at 9 mm to 9.1 millimeters, and any increments therein, from the surface of the tip, where the front working channel opening is located. Accordingly, the ramp structure is positioned within the working channel proximal to the side channel exit at a distance of at least 7 mm from the front working channel exit, and more preferably 8 mm to 10 mm, or at least 0.3 mm proximal to the side working channel exit (i.e. closer to the endoscope handle than the tip). In another embodiment comprising a slim endoscope having a smaller diameter, the side working channel is preferably positioned on the circumference of the endoscope at a distance of 8.7-8.9 mm from the surface of the tip. In all such cases, the working channel may have an inner diameter of 2.8 mm to 6.5 mm.

In other embodiments, the distal end of the ramp is located in the working channel at least 0.3 mm proximal (closer to the handle) relative to the side channel exit. In other embodiments, the pivot point of the ramp is located in the working channel at least 0.3 mm proximal (closer to the handle) relative to the side channel exit. In other embodiments, the distal end of the ramp is located in the working channel a distance of 0.3 mm to 10 mm proximal (closer to the handle) relative to the side channel exit. In other embodiments, the pivot point of the ramp is located in the working channel a distance of 0.3 mm to 10 mm proximal (closer to the handle) relative to the side channel exit.

In embodiments, an operating wire is used to operate ramp 801 remotely by rotating it in a desired direction. In an embodiment, the operating wire extends from the ramp to the handle of endoscope assembly. In embodiments, an additional knob or a button on the handle provides a control interface to a physician to control ramp 801. In various embodiments, the control interface can be located on the handle, on a main control unit connected to the endoscope assembly, on a computer connected to the endoscope assembly, or on any other external control unit that may communicate with the operating wire.

FIG. 7 illustrates a control system to regulate the position of ramp/elevator section in accordance with an embodiment of the present specification. As shown in FIG. 7, a ramp 801 comprises a vertical section 801a coupled to a pivot 820. In an embodiment, the pivot 820 is coupled to a control knob 890 through a control wire 880. In an embodiment, the control knob 890 is located on the control handle portion of the endoscope assembly such that the user/physician can operate the control knob 890 to regulate the position of ramp

801. One of ordinary skill in the art would appreciate that there could be multiple ways to couple the control wire 880 with the pivot 820 such that on user instruction, the position of pivot can be changed which in turn can change the position of ramp 801. In embodiment, the endoscope assembly comprises any of the conventional pivot joint systems to couple the control wire 880 to the pivot 220. Pivot structures comprises any one of a pivot hinge joint, a pivot ball and socket joint, or a pivot pin and hole joint. In some embodiments the control wire 880 is coupled to the pivot 820 through hinges located at position 860 shown in the FIG. 7. In an embodiment of the present specification, the ramp 801 is placed between the working channel exit point 841 positioned on the proximal fluid channeling section 802 of the fluid channeling component 810 and a front section 808 of the distal fluid channeling section 804 as illustrated in FIG. 3A. Medical tools inserted into the working channel 840 from the rear portion of the fluid channeling component 810 exit from the opening 841 and thereafter pass through the ramp/elevator 801 in an embodiment.

In an embodiment, the control wire can be operated to regulate the position of pivot 820 and ramp 801 in both the forward and sideway directions. In another embodiment, the pivot 820 is coupled to the ramp 801 such that the angular position of ramp can be modified to enable the medical tools to exit at multiple angles to the long dimension of the endoscope device. According to some embodiments, the ramp 801 comprises slightly raised structures referred as side anchoring support 830 provided along an upper edge of walls of ramp 801 which guide the medical tool 801 to bend at an angle and exit the tip section through a side wall of the device. In an embodiment, the ramp 801 is in a retracted position wherein the pivot 820 is positioned substantially inside the wall 804a of distal channeling section 804 of the fluid channeling component 810 shown in FIG. 3A, FIG. 3B and FIG. 4. In this position the medical tool 870 exiting from the opening 841 of the working channel 840 does not come in contact of the ramp 801 and is enabled to travel in a straight direction and exit from the front portion of the distal tip. In an embodiment, the ramp 801 is in an extended or raised position wherein the pivot 820 is positioned substantially outside the wall 804a of distal channeling section 804 of the fluid channeling component 810 as shown in FIG. 5A, 5B and FIG. 6. In this position, the ramp 801 and the anchoring supports 830 are positioned such that the medical tool bends at substantially 90 degree angle and exit the endoscope device from a side wall. While only two positions of the ramp are discussed in detail here, the control system described for pivot 820 and ramp 801 is configured such that the movement of ramp 801 can be controlled in multiple ways, including forward, backward, sideways, or in incremental angular shifts, to enable the medical tool to exit at a variety of angles from either the front portion or through a side portion/wall of the tip section of the endoscope device.

In some embodiments, movement of ramp 801 is automatically controlled by a computer program, or a predefined electronic signal. In embodiments, ramp 801 is adapted to operate with working channels of different dimensions, such as and not limited to working channel diameters ranging from 2.3 millimeters (mm) to 7 mm. Dimensions may vary on the basis of an application of the scope.

One of ordinary skill in the art would appreciate that the ramp 801 and the corresponding pivot can be manufactured with any known materials or alloys which are acceptable for use in medical applications. In an embodiment the ramp and the pivot section are manufactured with stainless steel.

FIG. 4 illustrates a medical tool 870 guided by ramp 801 to exit the front channel opening through working channel 840 in accordance with some embodiments. As shown in the FIG. 4, the position of ramp 801 is adjusted such that a pivot coupled to the ramp 801 is largely positioned on the inside of fluid channeling component 810; as a result, ramp 801 is in a position that allows the medical tool 870 to extend into the forward direction without bending. Thus, in this position, the ramp allows for the medical tool to exit at an angle of substantially zero degrees relative to the long dimension towards the front portion of the device. In this embodiment, the medical tool exits from the front end of the distal section of the endoscope assembly. In an embodiment, the position of ramp is adjusted by the physician through a control mechanism coupled to the handle section of the endoscope assembly as described in FIG. 7. In embodiments, the angle of exit of the medical tool 870 from the front end of the distal section is not exactly zero degrees relative to the long dimension towards the front portion of the device and the ramp is enabled to exit the front end of the distal tip at an acute angle relative to the long dimension of the device depending on the positioning and structure of working channel opening on the front portion of the distal tip.

FIGS. 5A and 5B illustrate two different views of an alternative position of ramp 801, in accordance with an embodiment. In this embodiment, the pivot 820 is configured in a raised position below ramp 801. When pivot 820 is activated, it emerges from the inside wall 804a of distal channeling section 804 of the fluid channeling component 810 such that ramp 801 is raised and repositioned in a way that it guides medical tool 801 (referring to FIG. 6) to exit the distal portion of tip section 800 through a side wall of the device. A side anchoring support 830 provided along an upper edge of walls of ramp 801 guides the medical tool 801 to bend at an angle and exit the tip section through a side wall of the device. In an embodiment, the ramp 801 and the side anchoring support 830 are adjusted such that the medical tool bends at substantially a 90 degree angle and exits the side wall of the of tip section 800 in a direction perpendicular to the long dimension of the endoscope. In alternate embodiments, the positions of ramp 801 and side anchoring support 830 can be adjusted to enable the medical device to exit at any other angle to the long dimension of the endoscope device. In an embodiment, the side anchoring support 830 is configured such that it also provides stability to medical tool 870 during a procedure. Side anchoring support 830 holds medical tool 870 in place and provides support to its sides while it is inserted through working channel 840 and is guided towards different directions.

Ramp 801 is controlled, in an embodiment, via pivot 820 which is used to guide or direct the exit of a medical tool 870 inserted through working channel 840 of endoscope assembly. The direction of medical tool 870 can be altered such that it may exit from either front panel 820, or through a side wall of the tip section 800 of endoscope assembly. The direction of medical tool 870 may be varied between angles from zero degrees to 90 degrees or more, to exit from working channel openings in the front or the side of tip section 800. Viewing elements, such as viewing element 816 on the front and viewing element 816b on the side, provide a view of medical tool 870 exiting in either direction.

FIG. 6 illustrates medical tool 870 guided by ramp 801 to exit from a side wall, according to some embodiments. As shown in FIG. 6, the pivot 820 is activated to raise ramp 801 such that medical tool 870, after exiting from the working channel 840, is bent and guided to exit distal part of tip section 800 from a side wall of the endoscope device. It should be appreciated that, typically, a tip cover such as the tip cover 300 shown in FIG. 1 covers the fluid channeling component 810 and the circuit board 850. The medical tool 870 exits from openings provided on the front panel or side walls of such a tip cover.

In various embodiments described in FIG. 3A to FIG. 6, the endoscope comprises a ramp structure that is coupled to an internal wall and can maneuver the medical tools towards the front portion or towards a side wall of the device. In an alternate embodiment of the present specification, the endoscope assembly is structured such that it comprises two working channels similar to the working channel 840 described in FIG. 3A wherein each working channel has at least one opening on the front portion of the distal tip section and at least one opening on the sidewall of the endoscope device. In addition, the system comprises a separate ramp structure for each working channel such that a first ramp structure enables operational access through the first working channel to the front portion and to one sidewall portion of the endoscope and the second ramp structure enables operational access through the second ramp structure to the front portion and to the opposite sidewall portion of the endoscope device.

In another embodiment, the endoscope assembly is structured such that the tip section comprises a fluid channeling component comprising a working channel with at least three exit openings. The working channel comprises at least one opening on the front portion and at least two openings on the opposite sidewalls. In an embodiment, the fluid channeling component is coupled to a ramp structure which is configured such that it can be positioned in the direction of either of the sidewalls of the endoscope device and in an embodiment, it can direct the medical device inserted through the working channel to either exit from the front portion or exit from either of the two openings on the opposite sidewalls of the device.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An endoscope assembly having a distal tip section, the assembly comprising:
   an electronic circuit board assembly comprising:
      a front-pointing viewing element at a front wall of the distal tip section and having a first field of view, wherein the front-pointing viewing element includes at least one image sensor in the distal tip section; and
      a side-pointing viewing element on at least one side wall of the distal tip section and having a second field of view;
   a fluid channeling component including a proximal fluid channeling section and a distal fluid channeling section, wherein the fluid channeling component comprises:
      at least one fluid channel extending through the proximal fluid channeling section and the distal fluid channeling section; and
      a working channel configured for insertion of a medical tool into and through the distal tip section, wherein said working channel provides:
         a first exit for said medical tool, said first exit comprising a first opening in the front wall of the distal tip section, wherein the first opening is positioned such that when the medical tool is moved distally through the first opening the medical tool enters the first field of view; and
         a second exit for said medical tool, said second exit comprising a second opening in the at least one side wall of the distal tip section, wherein the second opening is separate from the first opening and positioned such that when the medical tool is moved through the second opening the medical tool enters the second field of view;
      a ramp structure, wherein a portion of said ramp structure is positioned proximal to said second exit within said working channel, thereby positioning said second exit between the first exit and the portion of the ramp structure, wherein said ramp structure is movable relative to an internal wall of the fluid channeling component, the ramp structure comprising:
         a ramp including a first section and a second section, wherein the first section includes a first planar portion that is positioned substantially parallel to the internal wall of the fluid channeling component when the ramp structure is in a first position, and wherein the second section includes a second planar portion that is substantially perpendicular to the internal wall of the fluid channeling component when the ramp structure is in the first position and in a second position;
         a side anchoring support extending from an edge of the second section of the ramp and extending at an obtuse angle relative to the second planar portion; and
         a pivot arm coupled to the ramp structure, wherein a position of the ramp structure may be modified by pivoting movement of the pivot arm to regulate a direction of exit of the medical tool from the distal tip section, and wherein the internal wall of the fluid channeling component includes a recess configured to receive the pivot arm, the recess being narrower than the ramp structure; and
      an actuator coupled to said pivot arm, wherein said actuator is configured to modify a position of said pivot arm and said ramp structure, wherein the actuator is configured to transition the ramp structure between the first position and the second position, wherein, in the first position, the pivot arm is within the recess, and wherein, in the second position, the pivot arm projects out of the recess; and
      a cover configured to fit over the electronic circuit board assembly and the fluid channeling component.

2. The endoscope assembly according to claim 1, wherein said ramp structure is adapted to be positioned in at least two different angles relative to the internal wall of the distal tip section by pivoting movement of the pivot arm.

3. The endoscope assembly according to claim 1, wherein at least a portion of said ramp structure has an L-shaped cross-section configured to hold and guide an external surface of the medical tool.

4. The endoscope assembly according to claim 1, wherein said actuator comprises a control wire coupled to the pivot arm at a first end of the control wire and to a control knob positioned on a handle section of the endoscope assembly at a second end of the control wire.

5. The endoscope assembly according to claim 1, wherein when said pivot arm is in the first position, the ramp structure is positioned to enable the medical tool to exit from the first exit of the distal tip section.

6. The endoscope assembly according to claim 1, wherein when said pivot arm is in the second position, the ramp structure is configured to receive and bend the medical tool to enable the medical tool to exit from the second exit.

7. The endoscope assembly according to claim 6, wherein when said pivot arm is in the second position, said medical tool exits from the second exit at an angle of approximately 90 degrees relative to a central longitudinal axis of the distal tip section.

8. The endoscope assembly according to claim 1, wherein said ramp structure further comprises a first curvilinear section and a second curvilinear section, and wherein an edge of the first section is connected to an edge of the second section to form a groove for receiving and guiding the medical tool to either the first exit or the second exit.

9. The endoscope assembly according to claim 1, wherein the first exit is configured to allow the medical tool to pass through the first exit and into the field of view of the image sensor of the front viewing element.

\* \* \* \* \*